(12) United States Patent
Ghoreyshi

(10) Patent No.: US 12,082,911 B2
(45) Date of Patent: Sep. 10, 2024

(54) CORE TEMPERATURE ESTIMATION FROM SKIN AND AMBIENT TEMPERATURE SENSORS USING A DYNAMIC MODEL

(71) Applicant: Verily Life Sciences LLC, South San Francisco, CA (US)

(72) Inventor: Atiyeh Ghoreyshi, San Francisco, CA (US)

(73) Assignee: VERILY LIFE SCIENCES LLC, Dallas, TX (US)

( * ) Notice: Subject to any disclaimer, the term of this patent is extended or adjusted under 35 U.S.C. 154(b) by 336 days.

(21) Appl. No.: 17/249,562

(22) Filed: Mar. 5, 2021

(65) Prior Publication Data

US 2021/0275030 A1 Sep. 9, 2021

Related U.S. Application Data

(60) Provisional application No. 62/986,438, filed on Mar. 6, 2020.

(51) Int. Cl.
*A61B 5/01* (2006.01)
*G01K 3/10* (2006.01)
(Continued)

(52) U.S. Cl.
CPC ................ *A61B 5/01* (2013.01); *G01K 7/427* (2013.01); *G01K 13/20* (2021.01); *G01K 3/10* (2013.01)

(58) Field of Classification Search
CPC .......... G01K 7/427; G01K 3/10; G01K 13/20; A61B 5/01
See application file for complete search history.

(56) References Cited

U.S. PATENT DOCUMENTS 11,517,203 B2* 12/2022 Reifman .................. A61B 5/01
2010/0280331 A1 11/2010 Kaufman et al.
(Continued)

FOREIGN PATENT DOCUMENTS

CN 106539566 A * 3/2017 ............. A61B 5/015
CN 110575181 12/2019
(Continued)

OTHER PUBLICATIONS

Translation of CN110575181A (Year: 2019).*
(Continued)

*Primary Examiner* — Mirellys Jagan
(74) *Attorney, Agent, or Firm* — Kilpatrick Townsend & Stockton LLP

(57) ABSTRACT

A temperature measurement device for determining a body temperature of a subject includes a first temperature sensor configured to measure a plurality of skin temperatures of the subject at a plurality of time instants, a second temperature sensor spaced apart from the first temperature sensor and configured to measure a plurality of ambient temperatures at the plurality of time instants, a thermal insulation material between the first temperature sensor and the second temperature sensor, a memory device configured to store the plurality of skin temperatures and the plurality of ambient temperatures, and a controller configured to estimate, using a prediction model, the body temperature of the subject based on the plurality of skin temperatures and the plurality of ambient temperatures.

18 Claims, 15 Drawing Sheets

(51) Int. Cl.
*G01K 7/42* (2006.01)
*G01K 13/20* (2021.01)

(56) References Cited

U.S. PATENT DOCUMENTS

| | | |
|---|---|---|
| 2013/0296735 A1 | 11/2013 | James et al. |
| 2017/0124528 A1 | 5/2017 | Chakra et al. |
| 2017/0332904 A1 | 11/2017 | Gannon et al. |
| 2018/0184902 A1 | 7/2018 | Meyerson et al. |
| 2018/0214057 A1 | 8/2018 | Schultz et al. |
| 2018/0225342 A1 | 8/2018 | Kulshreshtha et al. |
| 2018/0279965 A1 | 10/2018 | Pandit et al. |
| 2019/0046033 A1 | 2/2019 | Gannon et al. |
| 2019/0350462 A1 | 11/2019 | Biederman et al. |
| 2020/0275841 A1 * | 9/2020 | Telfort .................. A61B 5/0075 |
| 2021/0278290 A1 * | 9/2021 | Ghoreyshi ............. A61B 5/746 |

FOREIGN PATENT DOCUMENTS

| | | | |
|---|---|---|---|
| CN | 113854973 A | * | 12/2021 |
| CN | 114235210 A | * | 3/2022 |
| CN | 115112265 A | * | 9/2022 |
| KR | 101798227 B1 | * | 11/2017 |
| WO | 2018112401 | | 6/2018 |

OTHER PUBLICATIONS

International Application No. PCT/US2021/021043, International Search Report and Written Opinion, mailed May 25, 2021, 9 pages.
U.S. Appl. No. 17/249,564 , "Final Office Action", Dec. 14, 2022, 15 pages.
U.S. Appl. No. 17/249,564 , "Non-Final Office Action", Jun. 1, 2023, 15 pages.
International Patent Application No. PCT/US2021/021042 , "International Search Report and Written Opinion", May 20, 2021, 9 pages.

* cited by examiner

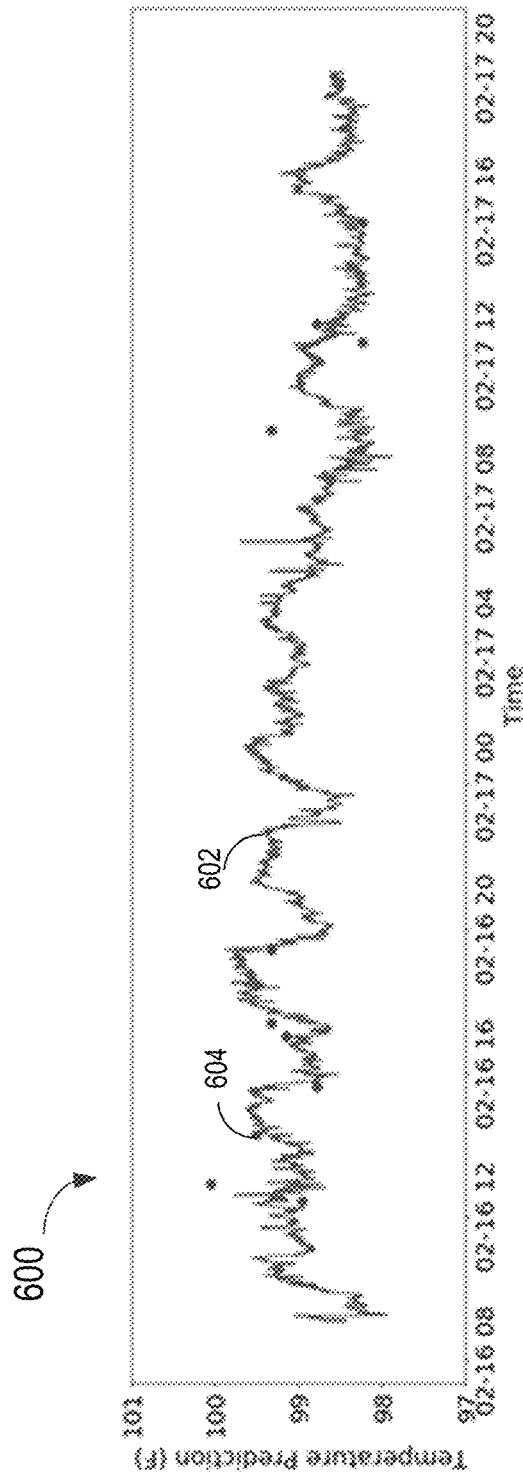
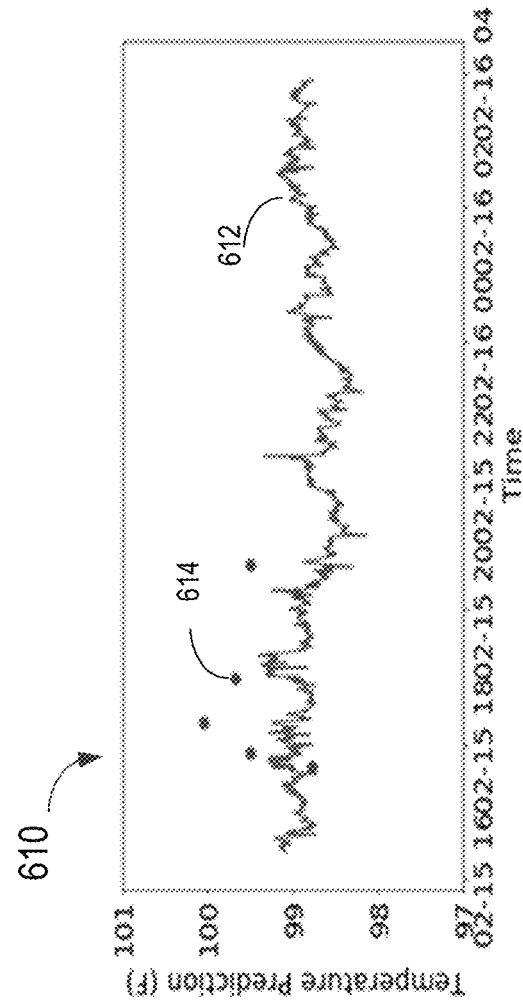
FIG. 6A
FIG. 6B

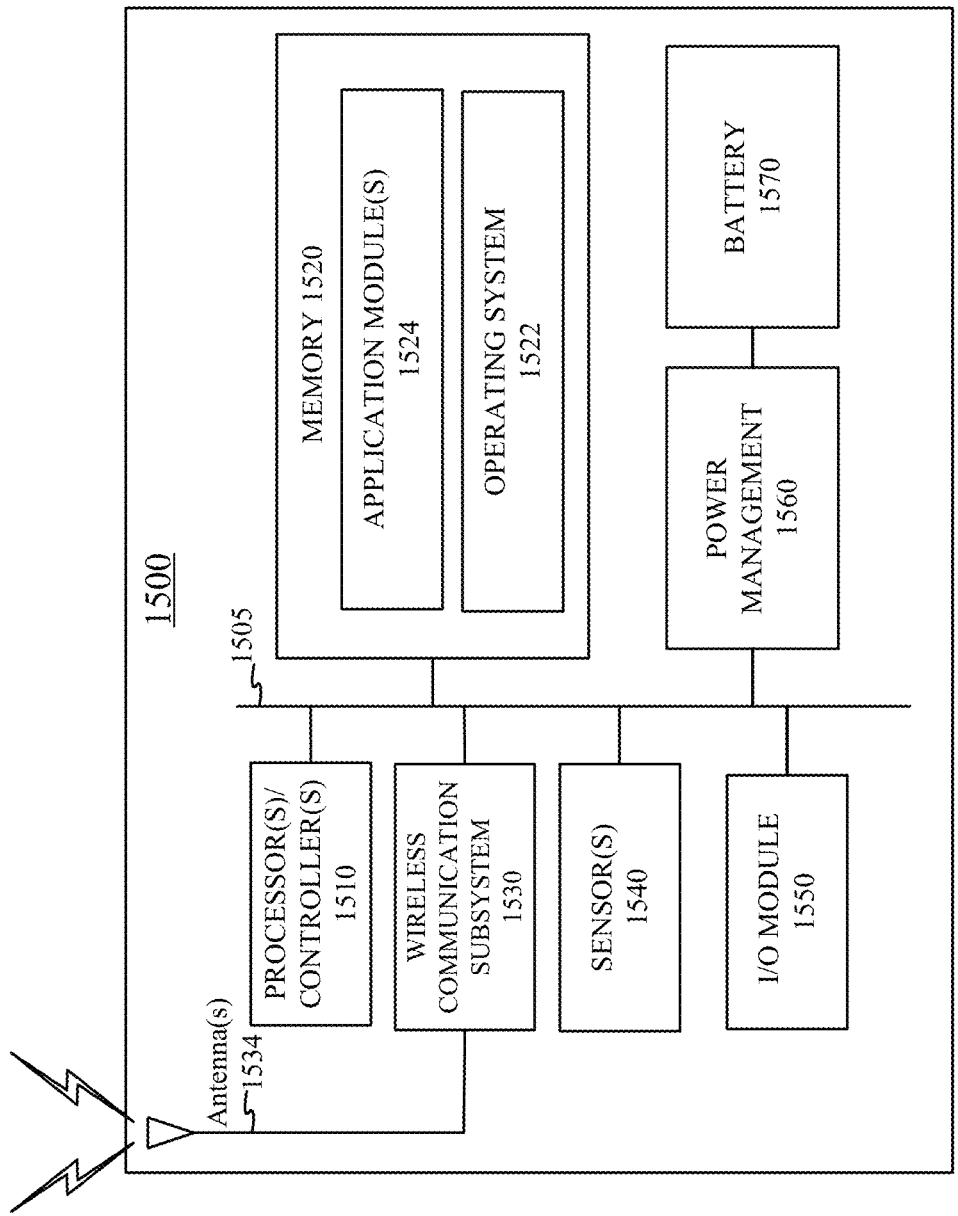

CORE TEMPERATURE ESTIMATION FROM SKIN AND AMBIENT TEMPERATURE SENSORS USING A DYNAMIC MODEL

CROSS-REFERENCE TO RELATED APPLICATIONS

This application claims priority to U.S. Provisional Patent Application No. 62/986,438, filed Mar. 6, 2020, titled "Core Temperature Estimation From Skin And Ambient Temperature Sensors Using A Dynamic Model," the entirety of which is hereby incorporated by reference.

FIELD

The present disclosure relates generally to non-invasive core body temperature measurements.

BACKGROUND

Assessment of a person's health often involves measuring the person's core body temperature. The person's core body temperature may be measured using invasive techniques that may involve taking measurements within the pulmonary artery, esophagus, rectum, or bladder. Non-invasive techniques may sometimes be used to measure the person's core body temperature. Examples of non-invasive techniques may include taking measurements in the mouth, under the armpit, in the ear canal, or at the temples of the head of the person. Non-invasive techniques are generally more convenient than invasive techniques, but may still be burdensome when frequent or periodic temperature measurements are taken. In addition, it can be more difficult to obtain accurate measurements of the core body temperature with existing non-invasive techniques.

SUMMARY

Techniques disclosed herein relate generally to non-invasive measurement of a person's core body temperature. Various inventive embodiments are described herein, including systems, modules, devices, components, methods, algorithms, non-transitory computer-readable storage media storing programs, code, or instructions executable by one or more processors, and the like. Those of ordinary skill in the art will realize that the following description is illustrative only and is not intended to be in any way limiting.

According to certain embodiments, a temperature measurement device for determining a body temperature of a subject may include a first temperature sensor configured to measure a plurality of skin temperatures of the subject at a plurality of time instants, a second temperature sensor spaced apart from the first temperature sensor and configured to measure a plurality of ambient temperatures at the plurality of time instants, a thermal insulation material between the first temperature sensor and the second temperature sensor, a memory device configured to store the plurality of skin temperatures and the plurality of ambient temperatures, and a controller configured to estimate, using a prediction model, the body temperature of the subject based on the plurality of skin temperatures and the plurality of ambient temperatures.

In some embodiments of the temperature measurement device, the prediction model may include a regression model that includes a set of regressors and corresponding weights. The regression model may include a nonlinear autoregressive exogenous (NARX) model. The set of regressors of the regression model may include skin temperatures and ambient temperatures measured at two or more past time instants. The set of regressors of the regression model may include each of the plurality of skin temperatures and the plurality of ambient temperatures raised to powers of two or more values. The weights of the regression model may be trained to minimize a mean square error.

In some embodiments, the temperature measurement device may also include a user interface device configured to receive at least one of a number of time instants in the plurality of time instants, a degree of polynomial in the regression model, or a measurement frequency of the first temperature sensor. The controller may be further configured to set the measurement frequency of the first temperature sensor. In some embodiments, the temperature measurement device may also include a user interface device configured to display the body temperature of the subject estimated by the controller or generate a signal indicating a high temperature event based on the body temperature of the subject. The temperature measurement device may be in a form of a wearable device or is embedded in a garment. In some embodiments, the temperature measurement device may further include a third temperature sensor spaced apart from the first temperature sensor and configured to measure a second plurality of skin temperatures of the subject at the plurality of time instants.

According to certain embodiments, a method of determining a body temperature of a subject may include measuring a plurality of skin temperatures of the subject at a plurality of time instants by a first temperature sensor, measuring a plurality of ambient temperatures at the plurality of time instants by a second temperature sensor spaced apart from the first temperature sensor, storing the plurality of skin temperatures and the plurality of ambient temperatures in a memory device, obtaining the plurality of skin temperatures and the plurality of ambient temperatures by a controller from the memory device, and determining the body temperature of the subject based on the plurality of skin temperatures and the plurality of ambient temperatures by the controller based on a prediction model.

In some embodiments, the prediction model may include a regression model that includes a set of regressors and corresponding weights. The regression model may include a nonlinear autoregressive exogenous (NARX) model. The set of regressors of the regression model may include skin temperatures and ambient temperatures measured at two or more past time instants. The set of regressors of the regression model may include each of the plurality of skin temperatures and the plurality of ambient temperatures raised to powers of two or more values. In some embodiments, the method may also include receiving, by a user interface device, at least one of a number of time instants in the plurality of time instants, a degree of polynomial in the regression model, or a measurement frequency of the first temperature sensor. In some embodiments, the method may also include at least one of displaying the body temperature of the subject determined by the controller, or generating a signal indicating a high temperature event based on the body temperature of the subject.

According to certain embodiments, a non-transitory computer-readable storage medium may store instructions executable by one or more processors. The instructions, when executed by the one or more processors, may cause the one or more processors to perform operations including obtaining a plurality of skin temperatures of a subject measured at a plurality of time instants, obtaining a plurality of ambient temperatures measured at the plurality of time instants, and determining a body temperature of the subject based on the plurality of skin temperatures and the plurality of ambient temperatures based on a regression model that includes a set of regressors and corresponding weights. In some embodiments, the regression model may include a nonlinear autoregressive exogenous (NARX) model, the set of regressors of the regression model may include skin temperatures and ambient temperatures measured at two or more past time instants, and the set of regressors of the regression model may include each of the plurality of skin temperatures and the plurality of ambient temperatures raised to powers of two or more values.

According to certain embodiments, a system may include a temperature measurement device configured to measure a plurality of body temperatures of a subject at a plurality of time instants in a time window, and a memory device configured to store the plurality of body temperatures. The system may also include a controller configured to obtain the plurality of body temperatures, determine a percentile value of the plurality of body temperatures at a first percentile, and generate an alert signal indicating that the percentile value of the plurality of body temperatures at a first percentile is greater than a threshold temperature value. The system may further include a user interface device configured to generate, based on the alert signal, a notification signal to a user of the system. The system may be in a form of a wearable device or is embedded in a garment.

In some embodiments, the user interface device may be further configured to receive at least one of a duration of the time window, the first percentile, the threshold temperature value, or a measurement frequency of the temperature measurement device. In some embodiments, the first percentile includes a 90% percentile. The controller may be further configured to set the temperature measurement device to measure at the measurement frequency. The duration of the time window may be longer than 30 minutes.

In some embodiments, the temperature measurement device may include a first temperature sensor configured to measure a plurality of skin temperatures of the subject at a set of time instants, a second temperature sensor spaced apart from the first temperature sensor and configured to measure a plurality of ambient temperatures at the set of time instants, a thermal insulation material between the first temperature sensor and the second temperature sensor, and a processing unit configured to estimate, using a prediction model, the plurality of body temperatures of the subject based on the plurality of skin temperatures and the plurality of ambient temperatures. The prediction model may include a regression model that includes a set of regressors and corresponding weights. The regression model may include a nonlinear autoregressive exogenous (NARX) model. The set of regressors of the regression model may include skin temperatures and ambient temperatures measured at two or more past time instants. The set of regressors of the regression model may include each of the plurality of skin temperatures and the plurality of ambient temperatures raised to powers of two or more values. The user interface device may be further configured to receive at least one of a number of time instants in the plurality of time instants, a degree of polynomial in the regression model, or a measurement frequency of the first temperature sensor.

According to certain embodiments, a method may include obtaining a plurality of body temperatures of a subject measured at a plurality of time instants in a time window, determining a percentile value of the plurality of body temperatures at a first percentile, generating an alert signal indicating that the percentile value of the plurality of body temperatures at the first percentile is greater than a threshold temperature value, and generating, based on the alert signal, a notification signal to a user, the notification signal indicating a high temperature event.

In some embodiments, the method may also include receiving at least one of a duration of the time window, the first percentile, the threshold temperature value, or a measurement frequency of a temperature measurement device that measures the plurality of body temperatures. The first percentile may include a 0% percentile, a 90% percentile, or a 100% percentile. In some embodiments, the method may also include setting the temperature measurement device to measure at the measurement frequency.

According to certain embodiments, a non-transitory computer-readable storage medium may store instructions executable by one or more processors. The instructions, when executed by the one or more processors, may cause the one or more processors to perform operations including obtaining a plurality of body temperatures of a subject measured at a plurality of time instants in a time window, determining a percentile value of the plurality of body temperatures at a first percentile, generating an alert signal indicating that the percentile value of the plurality of body temperatures at the first percentile is greater than a threshold temperature value, and generating, based on the alert signal, a notification signal to a user, the notification signal indicating a high temperature event. The operations may further include receiving at least one of a duration of the time window, the first percentile, or the threshold temperature value. The first percentile may include a 90% percentile.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification. This summary is neither intended to identify key or essential features of the claimed subject matter, nor is it intended to be used in isolation to determine the scope of the claimed subject matter. The subject matter should be understood by reference to appropriate portions of the entire specification of this disclosure, any or all drawings, and each claim. The foregoing, together with other features and examples, will be described in more detail below in the following specification, claims, and accompanying drawings.

BRIEF DESCRIPTION OF THE DRAWINGS

The accompanying drawings, which are incorporated into and constitute a part of this specification, illustrate one or more examples and, together with the description of the examples, serve to explain the principles and implementations of the examples.

FIG. 6A is a zoom-in view of the diagram shown in FIG. 5 according to certain embodiments.

FIG. 6B is another zoom-in view of the diagram shown in FIG. 5 according to certain embodiments.

FIG. 15 illustrates an example of an electronic system of a temperature measurement device according to certain embodiments.

Figure 1:
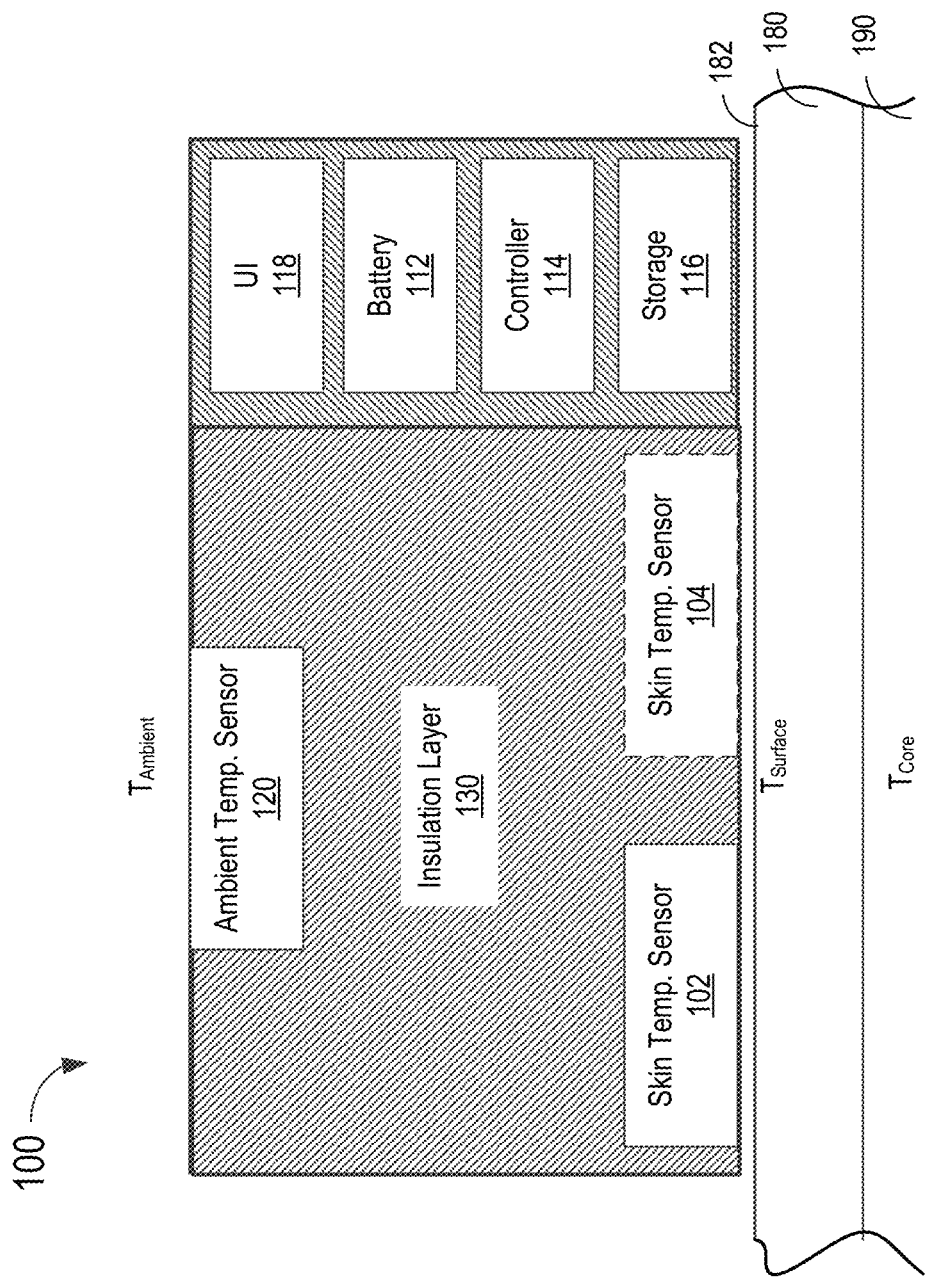
FIG. 1 illustrates an example of a temperature measurement device according to certain embodiments.

The figures depict embodiments of the present disclosure for purposes of illustration only. One skilled in the art will readily recognize from the following description that alternative embodiments of the structures and methods illustrated may be employed without departing from the principles, or benefits touted, of this disclosure.

In the appended figures, similar components and/or features may have the same reference label. Further, various components of the same type may be distinguished by following the reference label by a second label that distinguishes among the similar components. If only the first reference label is used in the specification, the description is applicable to any one of the similar components having the same first reference label irrespective of the second reference label.

DETAILED DESCRIPTION

Techniques disclosed herein relate generally to non-invasive core body temperature measurements. Various inventive embodiments are described herein, including systems, modules, devices, components, methods, non-transitory computer-readable storage media storing programs, code, or instructions executable by one or more processors, and the like.

Core body temperature may be a useful indicator of a person's health condition. Non-invasive techniques for core body temperature measurement, such as measuring temperatures in the mouth, under the armpit, in the ear canal, or at the temples of the head, are generally more convenient than invasive techniques, but many of these non-invasive techniques may still be burdensome when frequent or continuous temperature measurements are taken. In addition, many non-invasive techniques may not accurately measure the core body temperature below the skin due to, for example, the thermal resistance of the skin that prevents effective conduction of heat from the core to the skin surface, and the effects of the ambient environment (e.g., ambient air temperature that may be different from the skin temperature and the core body temperature). As a result, the temperature at the skin surface may be several degrees (° C.) lower than the core body temperature.

According to certain embodiments, a wearable non-invasive core body temperature measurement device may include a skin temperature sensor that measures the temperature of a person's skin and an ambient temperature sensor that measures the ambient temperature. The device may also include a processor that uses the present and past measurement results of the skin temperature sensor and the ambient temperature sensor to determine the core body temperatures or other body temperatures that may be different from the skin temperature, such as temperatures in the mouth. For example, an autoregressive model may be used to estimate the core body temperature based on the present and past measurement results.

The temperature measurement devices may be used for different applications, such as flu, fertility, oncology, and the like, and may be used to measure temperature of different types of people, such as men, women, adults, babies, and the like. The desired sensitivity may vary from application to application. For example, for oncology, it may be desirable to detect smaller changes in temperature, while the expected temperature increase from normal temperature may be much higher for flu. Therefore, for different applications, different parameters or models may be used for estimating the core body temperature.

In some embodiments, the temperature measurement devices may be able to generate alarm messages or notifications to indicate certain abnormal conditions. For different applications, different criteria may be used for determining whether to send a message or notification. For example, the decision may be made based on different durations of time considered, different percentiles of data points, different temperature thresholds, and the like. In some embodiments, the different criteria may be pre-set or dynamically set by an external device through a user interface device. In this way, the temperature measurement devices may be customized for different patients and different applications. In some embodiments, the temperature measurement devices may be set to operate in a lower power mode for applications that do not need high sensitivity or continuous measurements.

In the following description, for the purposes of explanation, specific details are set forth in order to provide a thorough understanding of examples of the disclosure. However, it will be apparent that various examples may be practiced without these specific details. For example, devices, systems, structures, assemblies, methods, and other components may be shown as components in block diagram form in order not to obscure the examples in unnecessary detail. In other instances, well-known devices, processes, systems, structures, and techniques may be shown without necessary detail in order to avoid obscuring the examples. The figures and description are not intended to be restrictive. The terms and expressions that have been employed in this disclosure are used as terms of description and not of limitation, and there is no intention in the use of such terms and expressions of excluding any equivalents of the features shown and described or portions thereof. The word "example" is used herein to mean "serving as an example, instance, or illustration." Any embodiment or design described herein as "example" is not necessarily to be construed as preferred or advantageous over other embodiments or designs.

Assessment of a person's health condition often involves measuring the person's core body temperature. Invasive techniques for determining the core body temperature may include taking measurements within the pulmonary artery, esophagus, rectum, or bladder. Non-invasive techniques may include taking temperature measurements in the mouth, under the armpit, in the ear canal, or at the temples of the head. Non-invasive techniques are generally more convenient than invasive techniques, but can still be burdensome when frequent temperature measurements are taken. Some non-invasive techniques may involve measuring temperature at the surface of the skin. However, a temperature measurement at the skin surface may not accurately reflect the core body temperature below the skin. For example, the thermal resistance of the skin may prevent effective conduction of heat from the core to the skin surface. Additionally, the ambient environment (e.g., air temperature and air flow) may affect the temperature measurement at the skin surface. As such, the temperature at the skin surface may be several degrees (° C.) lower than the core body temperature due to the thermal resistance of the skin and the effects of the ambient air.

According to certain embodiments, to accurately estimate the core body temperature based on temperature measurements taken non-invasively at the skin surface, the effects of the ambient temperature may be accounted for, alone or in combination with techniques that take into consideration the effects of the thermal resistance of the skin on the temperature measurements. In one illustrative embodiment, a wearable device may include a skin temperature sensor that measures the temperature of a person's skin, an ambient temperature sensor that measures the ambient temperature, and a processing unit that implements a regression model to estimate the core body temperature based on present and past measurement results of the skin temperature sensor and the ambient temperature sensor.

FIG. 1 illustrates an example of a temperature measurement device 100 according to certain embodiments. Temperature measurement device 100 may be in the form of a wearable device, such as a patch, a button, a wrist band, a watch, a head band, and the like. Temperature measurement device 100 may be positioned on a surface 182 of a person's skin 180, where temperature measurement device 100 may make frequent, non-invasive, and accurate measurement of the temperature ($T_{Core}$) of the person's core 190 under skin 180.

In the example illustrated in FIG. 1, temperature measurement device 100 may include one or more skin temperature sensors, such as skin temperature sensor 102 and skin temperature sensor 104. Skin temperature sensor 102 or skin temperature sensor 104 may be located close to a surface of temperature measurement device 100 such that, when temperature measurement device 100 is attached to skin 180 of the person, the sensing elements of skin temperature sensor 102 and/or skin temperature sensor 104 may be in contact with or close to surface 182 of skin 180 to measure the skin temperature of the person. Temperature measurement device 100 may also include one or more ambient temperature sensors, such as an ambient temperature sensor 120, positioned at a distance away from skin temperature sensor 102 and skin temperature sensor 104. The one or more ambient temperature sensors may be isolated from the one or more skin temperature sensors by an insulation layer 130. The one or more ambient temperature sensors and the one or more skin temperature sensors may each include, for example, a thermistor, a resistance temperature detector, a thermocouple, a semiconductor (e.g., silicon) temperature sensor, or the like, and may include an analog-to-digital converter to generate digital outputs.

Temperature measurement device 100 may also include other electronic components and circuits, such as a controller 114, a storage device 116, a user interface device 118, and a battery 112. Temperature measurement device 100 may include other electronic circuits, such as capacitors, resistors, inductors, transducers, power management circuits, and the like. Controller 114 may include one or more processing units, and may be used to control the operations of the one or more ambient temperature sensors, the one or more skin temperature sensors, storage device 116, user interface device 118, and the like. Controller 114 may also receive measurement results from the one or more ambient temperature sensors and the one or more skin temperature sensors or from storage device 116, and determine the core body temperature based on the measurement results. For example, controller 114 may use a regression model and the measurement results of the ambient temperatures and the skin temperatures to estimate the core body temperature.

Storage device 116 may include one or more memory devices. The one or more memory devices may include volatile and/or non-volatile memory devices. Storage device 116 may store instructions to be executed by controller 114, the model (e.g., weights or other parameters) used by controller 114 to estimate the cord body temperatures, measurement results from the ambient temperature sensors and the skin temperature sensors, estimated core body temperature, and the like.

Battery 112 may include a button or coin cell battery, such as a lithium, silver, alkaline, or nickel cell battery. Battery 112 may be chargeable or non-chargeable. User interface device 118 may be used to receive instructions or information from users or other devices, and provide information to users or other devices. User interface device 118 may include various input and/or output devices, such as an LCD or LED display, a speaker, a button, a wired or wireless communication subsystem, or the like. For example, user interface device 118 may include a wireless communication subsystem that utilizes various wireless communication standards or protocols, such as cellular communication standards (e.g., 2G, 3G, 4G, or 5G cellular communication standards), Wi-Fi, WiMax, Bluetooth, Bluetooth Low Energy (BLE), ZigBee, and the like. In another example, user interface device 118 may include a speaker that may generate an alarm signal when, for example, the measurement temperature is above a threshold value.

Figure 2:
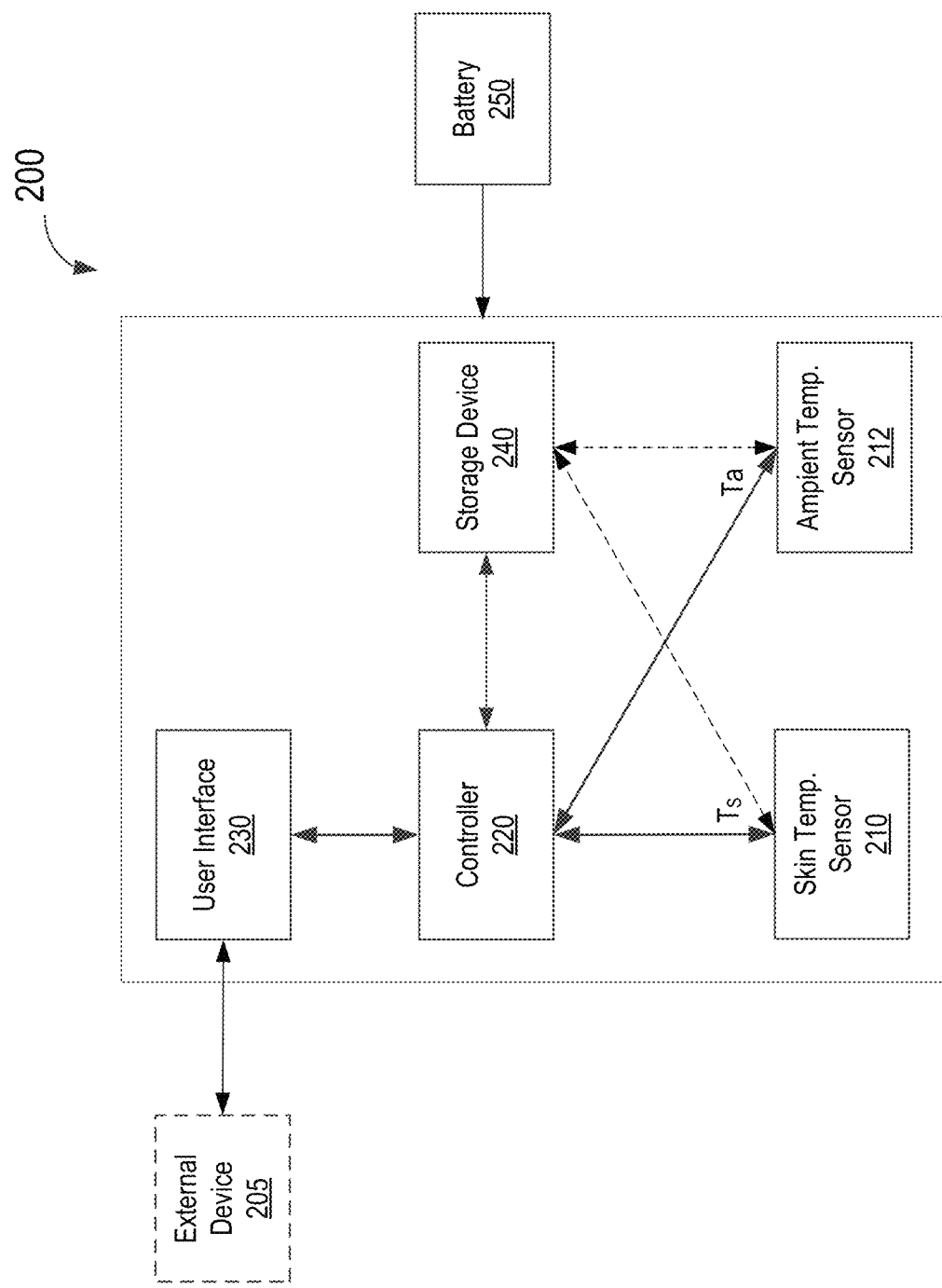
FIG. 2 illustrates examples of electrical connections between components of an example of a temperature measurement device according to certain embodiments.

FIG. 2 illustrates examples of electrical connections between components of an example of a temperature measurement device 200, such as temperature measurement device 100, according to certain embodiments. In the illustrated example, temperature measurement device 200 may include a skin temperature sensor 210, an ambient temperature sensor 212, a controller 220, one or more user interface devices 230, a storage device 240, and a battery device 250. Battery device 250 may be similar to battery 112, and may be used to provide, for example, through a power management or converting circuit, electrical power to other electrical components in temperature measurement device 200.

Skin temperature sensor 210 and ambient temperature sensor 212 may be similar to skin temperature sensor 102 and ambient temperature sensor 120, respectively. Skin temperature sensor 210 may measure a skin temperature $T_s$ on a surface of a person's skin. Ambient temperature sensor 212 may measure an ambient temperature $T_a$. Measurement results of skin temperature sensor 210 and ambient temperature sensor 212 may be provided to controller 220 or may be saved in storage device 240 directly or through controller 220. Controller 220 may control the operations of skin temperature sensor 210 and ambient temperature sensor 212, such as the sampling frequency. Controller 220 may obtain present and past measurement results of skin temperature sensor 210 and ambient temperature sensor 212 from storage device 240 and/or skin temperature sensor 210 and ambient temperature sensor 212, and estimate a core body temperature based on the present and past measurement results. Controller 220 may communicate with users or external devices 205 through user interface device 230, which may be similar to user interface device 118 described above. For example, controller 220 may provide estimated results of the core body temperature through user interface device 230, such as sending an alarm message through a speaker or a light source (e.g., an LED). Controller 220 may also receive instructions or data from external device 205, such as parameters of the model used to estimate the core body temperature or the parameters used to determine whether an alarm message may need to be generated.

Various prediction models may be used by controller 220 to estimate the core body temperature based on skin temperature and ambient temperature measurement results. For example, a regression model, such as a linear regression model, a polynomial regression model, a lasso regression model, a ridge regression model, or an ElasticNet regression model, and the like, may be used to estimate the core body temperature based on skin temperature and ambient temperature measurement results. In some embodiments, other machine learning-based prediction models, such as a neural network model, may be used to estimate the core body temperature based on skin temperature and ambient temperature measurement results.

According to one embodiment, controller 220 may use an all zeros nonlinear autoregressive exogenous (NARX) model and present and past measurement results of skin temperature sensor 210 and ambient temperature sensor 212 to estimate a core body temperature. The NARX model may be described as:

$$T_c(t) = w_1 \times T_a(t) + w_2 \times T_s(t) + w_3 \times T_a(t-1) + w_4 \times T_s(t-1) \ldots$$
$$+ w_{(k+2)} \times T_s(t-m+1) + w_{(k+1)} \times T_s(t-m+1) + w_k \times T_a^2(t) + w_{(k+1)} \times T_s^2(t) + w_{(k+2)} \times T_a^2(t-1) + w_{(k+3)} \times T_s^2(t-1) + \ldots + w_i \times T_a^3(t) + w_{(i+1)} \times T_s^3(t) + w_{(i+2)} \times T_a^3(t-1) + w_{(i+3)} \times T_s^3(t-1) + \ldots + w_j \times T_a^n(t) + w_{(j+1)} \times T_s^n(t) + w_{(j+2)} \times T_a^n(t-1) + w_{(j+3)} \times T_s^n(t-1) + \ldots + c,$$

where $T_c(t)$ is the estimated core temperature at time t, $T_a(t)$ is the measured ambient temperature at time t, $T_s(t)$ is the measured skin temperature at time t, w's are weights of the NARX model, m is the number of past sensor readings (referred to as memory) used as regressors, n represents the highest power (referred to as power or degree) to which each regressor is raised, and c is the intercept of the NARX model.

The weights w's may be trained using training data that may include measured ambient temperatures $T_a(t)$, the measured skin temperature $T_s(t)$, and measure core body temperatures or other body temperatures that are different from skin temperatures, such as temperatures measured in the mouth of a person. The weights of the NARX model may be adjusted based on the differences between the core body temperatures or other body temperatures that are different from skin temperatures, and temperature $T_c(t)$ estimated using the NARX model. For example, the weights may be adjusted to achieve the minimum standard deviation of the prediction errors.

In some embodiments, past estimation data, such as $T_c(t-m)$, may also be used in a regression model to estimate current core body temperature. In some embodiments, the number (m) of past sensor readings used as regressors, and/or the highest power (n) to which each regressor is raised may be optimized or learned based on the training data.

Figure 3:
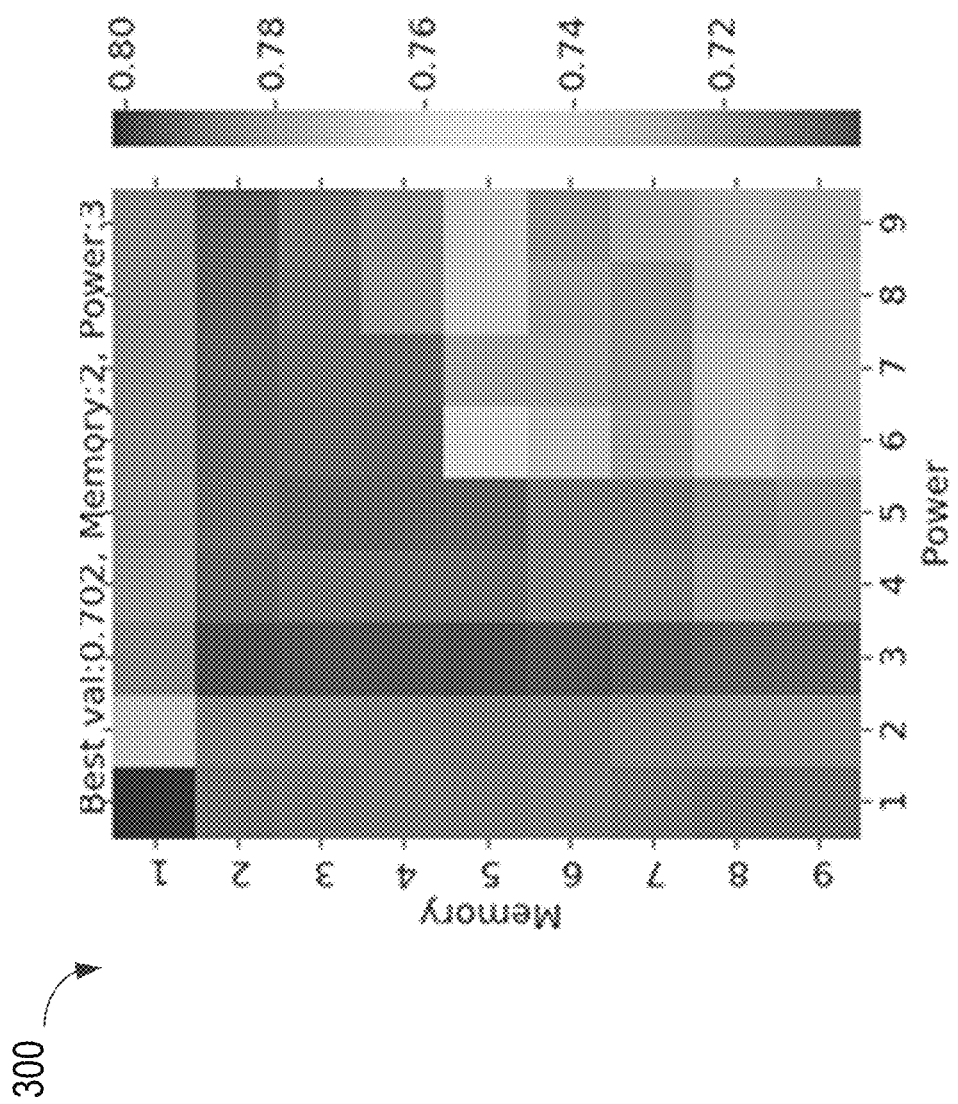
FIG. 3 illustrates an example of a grid search method for optimized memory and power parameters of a regression model according to certain embodiments.

FIG. 3 illustrates an example of a grid search method 300 for optimized memory and power parameters of a regression model according to certain embodiments. The memory and power parameters can be tuned over a range of memory and power values. For each combination of memory (m) and power (n) values, a leave-one-out cross validation may be used to train the model using some training data and to validate the model using other training data. Various statistics may be calculated based on estimated core body temperatures and measured core body temperatures (or temperature measured in the mouth). The statistics may include, for example, mean error, mean or median absolute error, standard deviation of error, $R^2$ statistics (or coefficient of determination) or variance accounted for (VAF), and the like. The best combination of memory and power parameters may be determined based on these statistics. For example, the standard deviation of the error or the VAF may be used to determine the best combination of memory and power parameters.

In the illustrated example, the power parameter (n) may be varied from one to 9, and the memory parameter (m) may be varied from 1 to 9 as well. For each combination of memory (m) and power (n) values, the standard deviation of the prediction error is plotted in a matrix 300, where the value of the standard deviation of the prediction error is represented by different colors. The combination of memory (m) and power (n) values which give the least standard-deviation of prediction error may be used in the regression model. In the example shown in FIG. 3, the standard-deviation of prediction error may be the lowest (e.g., about 0.72) when m=2 and n=3. Memory value (m) of 2 indicates that the current sensor reading and one past readings are used as regressors. Power value (n) of 3 indicates that the regressors are raised to the power of 2 and power of 3 to form additional regressors. A 10-fold cross-validation shows that the standard deviation of the error is about 0.8×F, the mean absolute error is about 0.6×F, and the $R^2$ or VAF is about 0.4, where F is the F-statistic value, for example, F=variation between sample means/variation within the samples.

In some embodiments, the frequency of the sensor readings may be optimized as well. For example, the optimum time interval between consecutive readings may be determined based on the training data. The frequency of the sensor readings and other settings of the temperature sensors, and the model (e.g., the memory and power values) may be pre-set or dynamically set by an external device through user interface device 118 or 230 described above.

Using the optimized model described above, the controller may more accurately determine the core body temperature based on measured skin temperatures and ambient temperatures. The temperature measurement devices utilizing the model for core body temperature estimation may be used to estimate core body temperature based on skin temperature measurements taken at different locations of a person's body.

Figure 4:
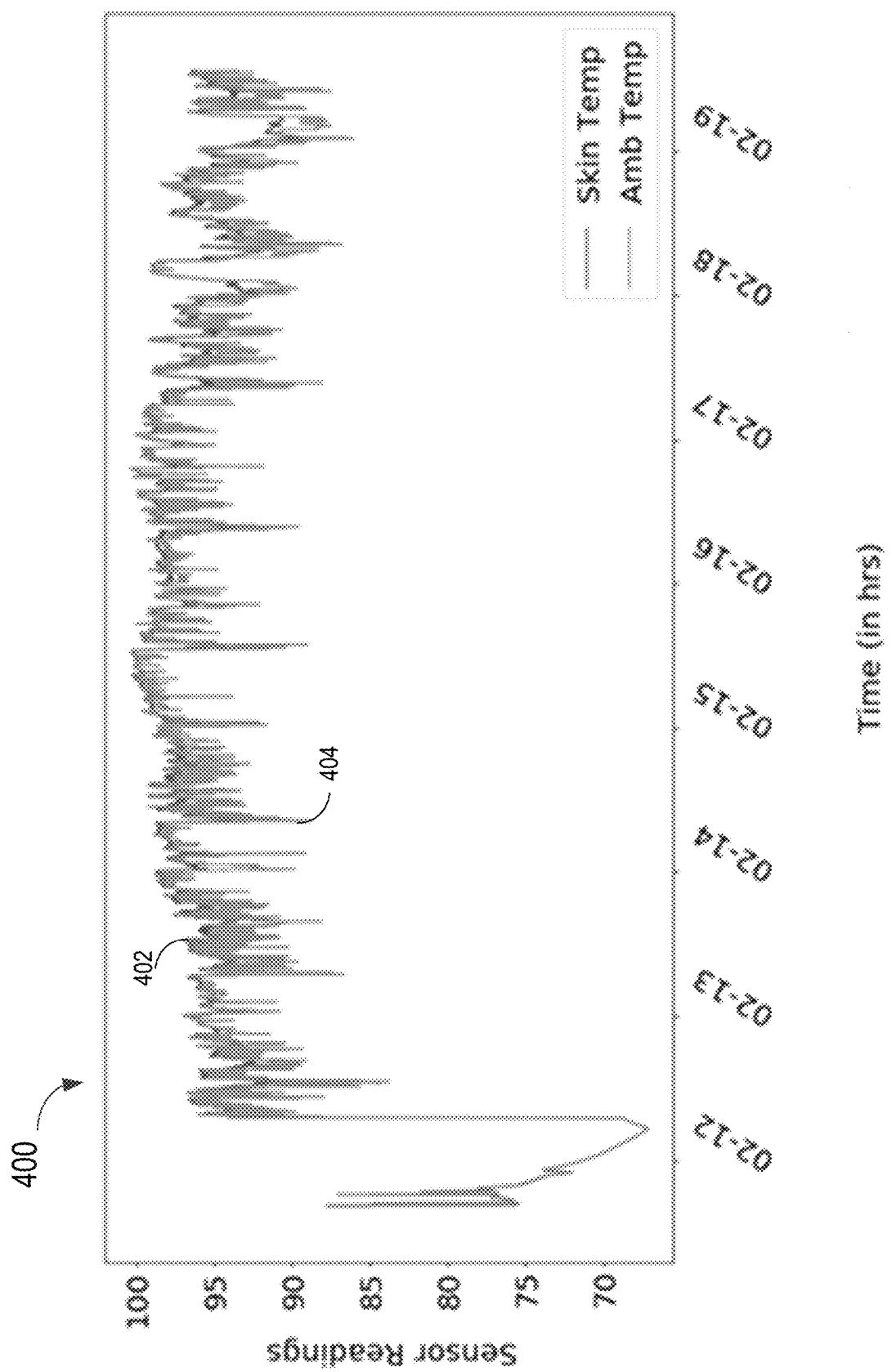
FIG. 4 includes a diagram illustrating examples of raw sensor readings recorded for a single subject over a week by a temperature measurement device described above according to certain embodiments.

FIG. 4 includes a diagram 400 illustrating examples of raw sensor readings recorded for a single subject over a week by a temperature measurement device described above according to certain embodiments. The raw sensor readings may include readings by a skin temperature sensor, such as skin temperature sensor 102, as shown by a curve 402. The raw sensor readings may also include readings by an ambient temperature sensor, such as ambient temperature sensor 120, as shown by a curve 404.

Figure 5:
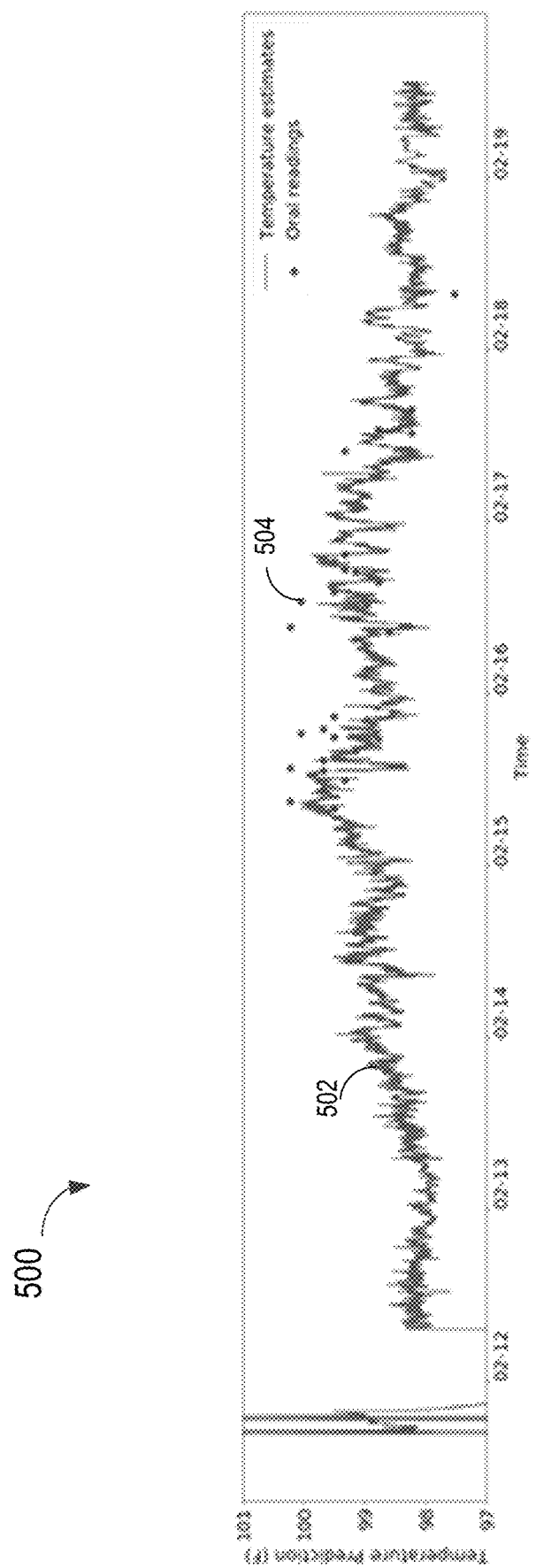
FIG. 5 includes a diagram illustrating examples of core body temperature estimated by a temperature measurement device described above according to certain embodiments.

FIG. 5 includes a diagram 500 illustrating examples of core body temperature estimated by a temperature measurement device described above according to certain embodiments. The core body temperature estimated by the temperature measurement device may be shown by a curve 502, which may be determined using a regression model and the raw sensor readings shown in FIG. 4. FIG. 5 also includes data points 504 representing temperatures measured in the subject's mouth at some time instants.

FIG. 6A is a zoom-in view 600 of diagram 500 of FIG. 5 according to certain embodiments. The core body temperature estimated by the temperature measurement device during a first time period may be shown by a curve 602, which may be determined using a regression model and the raw sensor readings shown in FIG. 4. FIG. 6A also includes data points 604 representing temperatures measured in the subject's mouth (referred to as oral readings) at some time instants. FIG. 6A shows that, in the illustrated first time period, the estimated core body temperature may match well with the temperatures measured in the subject's mouth.

FIG. 6B is another zoom-in view 610 of diagram 500 of FIG. 5 according to certain embodiments. The core body temperature estimated by the temperature measurement device during a second time period may be shown by a curve 612, which may be determined using a regression model and the raw sensor readings shown in FIG. 4. FIG. 6B also includes data points 614 representing temperatures measured in the subject's mouth at some time instants. FIG. 6B shows that, in the illustrated second time period, the estimated core body temperature may not match the temperatures measured in the subject's mouth. The mismatch may be due to the noisy oral readings as indicated by the large variations of data points 614 associated with the oral readings.

FIGS. 7A-7D illustrate examples of different implementations of the temperature measurement devices, such as temperature measurement device 100, described above according to certain embodiments. In the example illustrated in FIG. 7A, two temperature measurement devices 712 and 714 may be attached to a frame 710 for eyeglasses. For example, the temperature measurement devices 712 and 714 may be securely coupled to respective temples 716 and 718 of the frame 710 using fasteners, adhesive, tape, hook-and-loop fasteners, elastic bands, and/or the like. Temperature measurement devices 712 and 714 may be sufficiently small and lightweight so that the person can wear the frame 710 comfortably. Temperature measurement devices 712 and 714 may be positioned such that they can make full and consistent contact with skin surface areas 702 and 704 corresponding to the temples of the person's head, where the core body temperature $T_{Core}$ can be measured from the temporal arteries. Advantageously, temperature measurement devices 712 and 714 may provide two independent measurements of the core body temperature $T_{Core}$, which can be compared and/or averaged to help promote accuracy.

Figure 7A:
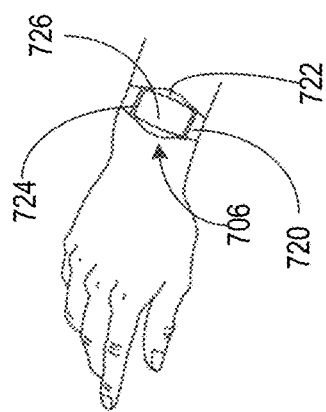
FIGS. 7A-7D illustrate examples of different implementations of the temperature measurement devices according to certain embodiments.
Figure 7B:
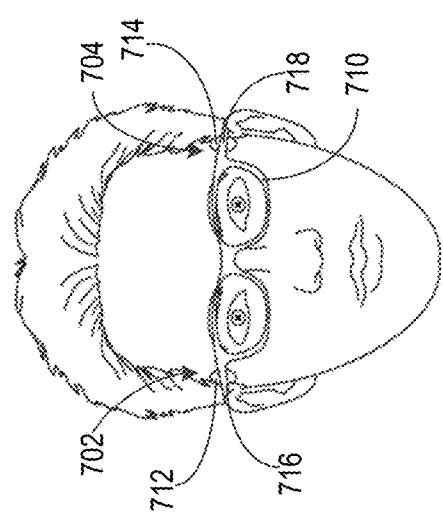

In the example illustrated in FIG. 7B, a temperature measurement device 722 may be combined with a wrist device 720, such as a watch or fitness band. Temperature measurement device 722 may be integrated with wrist device 720, where a housing 724 of wrist device 720 may house the components of temperature measurement device 722. Additionally, a user interface device 726 for wrist device 720 may act as the user interface device for temperature measurement device 722. When wrist device 720 is a fitness band, for example, the core body temperature $T_{Core}$ may be displayed with other types of fitness data, such as heart rate, calories burned, and the like. Furthermore, a battery for wrist device 720 can power temperature measurement device 722. Alternatively, temperature measurement device 722 may be coupled as a physically separate device to the back of wrist device 720. Wrist device 720 may position temperature measurement device 722 so that it can take measurements of the core body temperature $T_{Core}$ from a skin surface area 706 on the person's wrist. The fit of wrist device 520 can help press temperature measurement device 722 against the skin surface area 706 to achieve full and consistent contact.

Figure 7C:
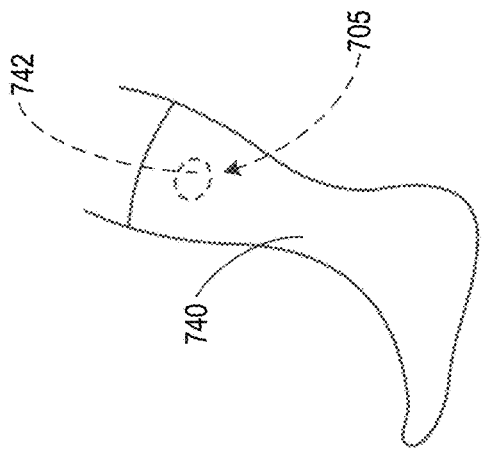

In the example shown in FIG. 7C, at least one temperature measurement device 732 may be combined with a wearable garment, such as a headband 730, or may be otherwise coupled to headband 730 by fasteners, adhesives, tape, hook-and-loop fasteners, and/or the like. Temperature measurement device 732 may be positioned such that it can take measurements of the core body temperature $T_{Core}$ from a skin surface area 708 on the person's forehead or temple. The tight fit of headband 730 may help press temperature measurement device 732 against the skin surface area 708 to achieve full and consistent contact.

Figure 7D:
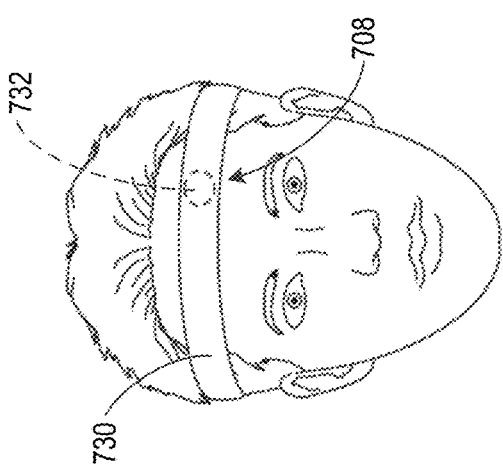

In the example shown in FIG. 7D, at least one temperature measurement device 742 may be combined with a sock 740 that is worn about the person's foot and ankle. Temperature measurement device 742 may be sewn into sock 740 and/or otherwise coupled to sock 740 by fasteners, adhesives, tape, hook-and-loop fasteners, and/or the like. Temperature measurement device 742 may be positioned so that it can take measurements of the core body temperature $T_{Core}$ from a skin surface area 705 near the person's ankle or foot. The tight fit of sock 740 can help press temperature measurement device 742 against the skin surface area to achieve full and consistent contact.

Even though not shown in FIGS. 7A-7D, one or more temperature measurement devices described above may be combined with any type of wearable devices. For example, in one embodiment, the temperature measurement device may be combined with headphones. One or more temperature measurement devices described above may also be combined with any type of clothing, also including, but not limited to, hats, gloves, shoes, undergarments, etc. The clothing can position the one or more temperature measurement devices on skin surface areas to measure the core body temperature $T_{Core}$ as described above. In different embodiments, the temperature measurement devices may use different models or different parameters to estimate the core body temperature, where the models and parameters may be optimized and/or trained as described above.

The temperature measurement devices described above may be used for different applications, such as flu, fertility, oncology, and the like, and may be used to measure temperature of different types of people, such as men, women, adults, babies, and the like. The desired sensitivity may vary from application to application. For example, for oncology, it may be desirable to detect smaller changes in temperature, while the expected temperature increase from normal temperature may be much higher for flu. Therefore, for different applications, different parameters or models may be used for estimating the core body temperature.

As described above, in some embodiments, the temperature measurement devices may be able to generate alarm messages or notifications to indicate certain abnormal conditions. For different applications, different criteria may be used for determining whether to send a message or notification. For example, the decision may be made based on different durations of time considered, different percentiles of data points, different temperature thresholds, and the like. In some embodiments, the different criteria may be pre-set or dynamically set by an external device (e.g., external device 205) through user interface device 118 or 230 described above. In this way, the temperature measurement devices may be customized for different patients and different applications. In some embodiments, the temperature measurement devices may be set to operate in a lower power mode for applications that do not need high sensitivity or continuous measurements.

In some embodiments, a static fever detection model may be used to detect fever based on the estimated core body temperature. For example, in some embodiments, a fever alert may be generated when the estimated temperature at a given time instant is greater than a certain threshold. In other words, fever alerts may be generated based on only the current temperature estimate.

Figure 8:
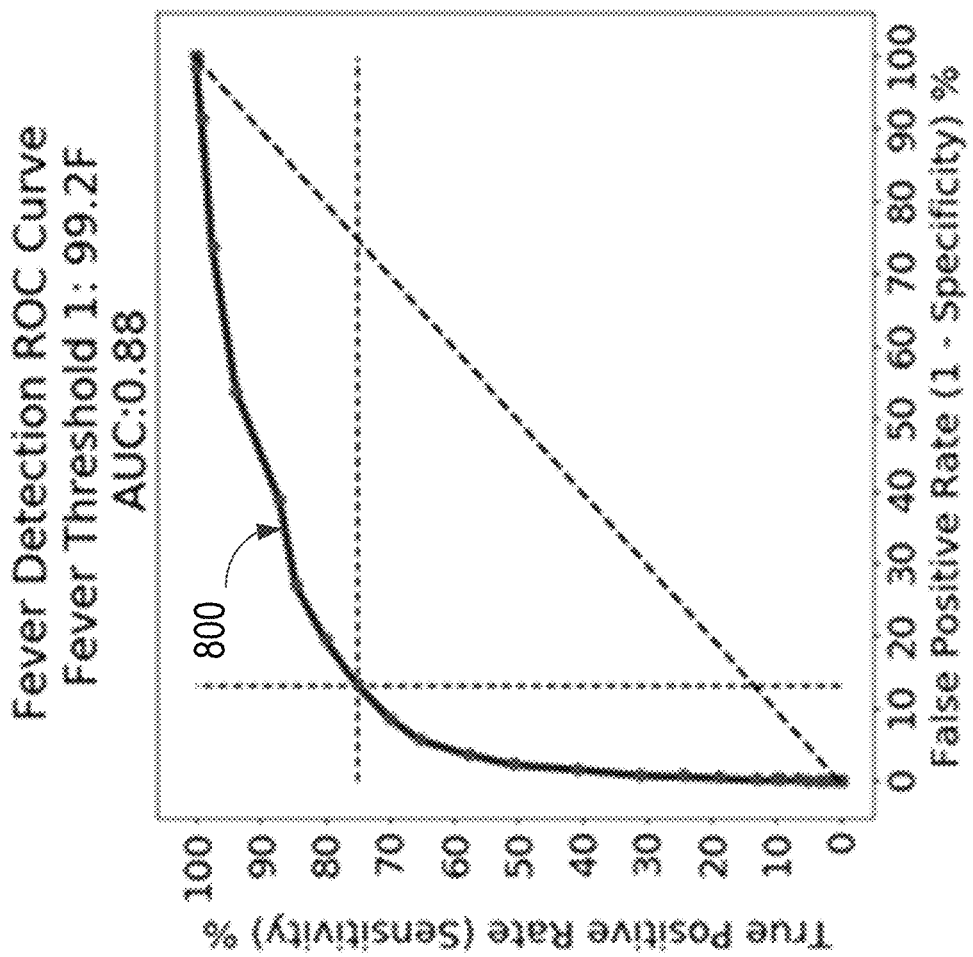
FIG. 8 illustrates an example of a receiver operating characteristic (ROC) curve for fever detection based on current estimated temperature according to certain embodiments.

FIG. 8 illustrates an example of a receiver operating characteristic (ROC) curve 800 for fever detection based on current estimated temperature according to certain embodiments. ROC curve 800 is a graphical plot that illustrates the diagnostic ability of a binary classifier system as its discrimination threshold is varied. The horizontal axis in FIG. 8 corresponds to false positive (FP) rate or (1-specificity), while the vertical axis corresponds to true positive (TP) rate or sensitivity. The sensitivity describes the ability of the model to correctly determine data points associated with high fever, and can be calculated according to sensitivity=TP/(TP+FN). The specificity describes the ability of the model to correctly determine data points not associated with high fever, and can be calculated according to specificity=TN/(TN+FP). TP (true positive) is the number of data points correctly identified as afflicted with high fever, TN (true negative) is the number of data points correctly identified as not afflicted with high fever, FP (false positive) is the number of data points incorrectly identified as afflicted with high fever, and FN (false negative) is the number of data points incorrectly identified as not afflicted with high fever.

In the example shown in FIG. 8, ROC curve 800 indicates that the maximum sum of sensitivity and specificity may be achieved when the threshold for high fever is set at 99.2° F. When the threshold for high fever is set at 99.2° F., the sensitivity of the fever detection model is about 0.76, and the specificity of the fever detection model is about 0.88.

In some embodiments, a dynamic fever alert model may use the core body temperature estimates over a time period to produce an alert when a certain statistic of the estimates in the time period exceeds a certain threshold. For example, the dynamic fever alert model may predict a fever by considering past temperature estimates over a time window of 60 minutes to 120 minutes. If a certain percentile (e.g., 90th percentile) of temperature estimates in the time window is above a certain threshold, a fever alert may be generated. If the percentile used is 0th percentile, all temperature estimates in the time window need to be greater than threshold to cause a fever alert. If the percentile used is 100th percentile, a fever alert may be generated as long as the maximum value in the time window is greater than the threshold.

Figures 9A, 9B, 9C:
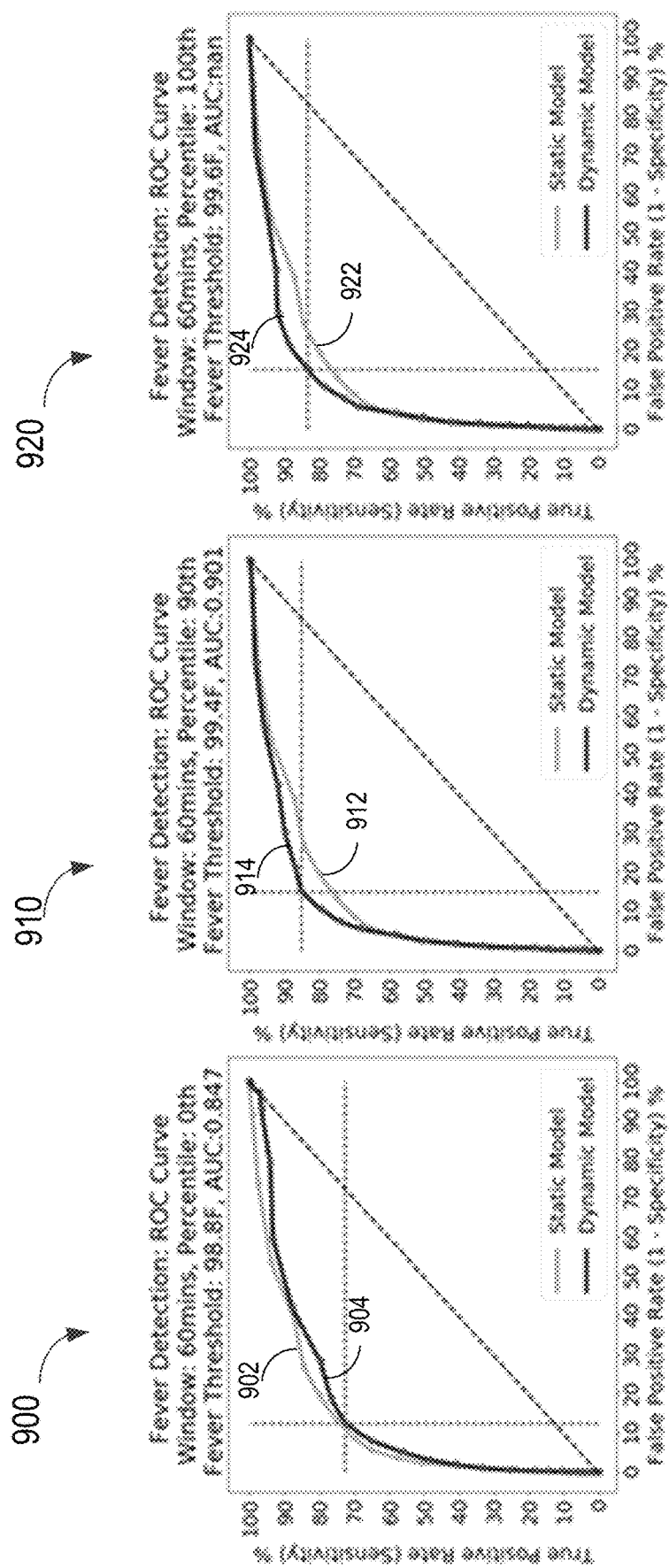
FIG. 9A includes a diagram showing examples of ROC curves for fever detection using a static fever alert model and a dynamic fever alert model according to certain embodiments.
FIG. 9B includes a diagram showing examples of ROC curves for fever detection using a static fever alert model and a dynamic fever alert model according to certain embodiments.
FIG. 9C includes a diagram showing examples of ROC curves for fever detection using a static fever alert model and a dynamic fever alert model according to certain embodiments.

FIG. 9A includes a diagram 900 showing examples of ROC curves for fever detection using a static fever alert model and a dynamic fever alert model according to certain embodiments. In FIG. 9A, an ROC curve 902 is generated using a static fever alert model as described above with respect to FIG. 8. An ROC curve 904 is generated using a dynamic fever alert model where the time window is 60 minutes and the 0th percentile is used to compare against the threshold temperature. The maximum sum of sensitivity and specificity may be achieved when the threshold for high fever is set at 98.8° F.

FIG. 9B includes a diagram 910 showing examples of ROC curves for fever detection using a static fever alert model and a dynamic fever alert model according to certain embodiments. In FIG. 9B, an ROC curve 912 is generated using a static fever alert model as described above with respect to FIG. 8. An ROC curve 914 is generated using a dynamic fever alert model where the time window is 60 minutes and the 90th percentile is used to compare against the threshold temperature. The maximum sum of sensitivity and specificity may be achieved when the threshold for high fever is set at 99.4° F.

FIG. 9C includes a diagram 920 showing examples of ROC curves for fever detection using a static fever alert model and a dynamic fever alert model according to certain embodiments. In FIG. 9C, an ROC curve 922 is generated using a static fever alert model as described above with respect to FIG. 8. An ROC curve 924 is generated using a dynamic fever alert model where the time window is 60 minutes and the 100th percentile is used to compare against the threshold temperature. The maximum sum of sensitivity and specificity may be achieved when the threshold for high fever is set at 99.6° F.

FIGS. 9A-9C indicate that the maximum sum of sensitivity and specificity may be achieved when the 90th percentile is used to compare against a threshold temperature set to 99.4° F. Under this setting, the sensitivity of the dynamic fever alert model is about 0.85, and the specificity of the dynamic fever alert model is about 0.84.

Figures 10A, 10B, 10C:
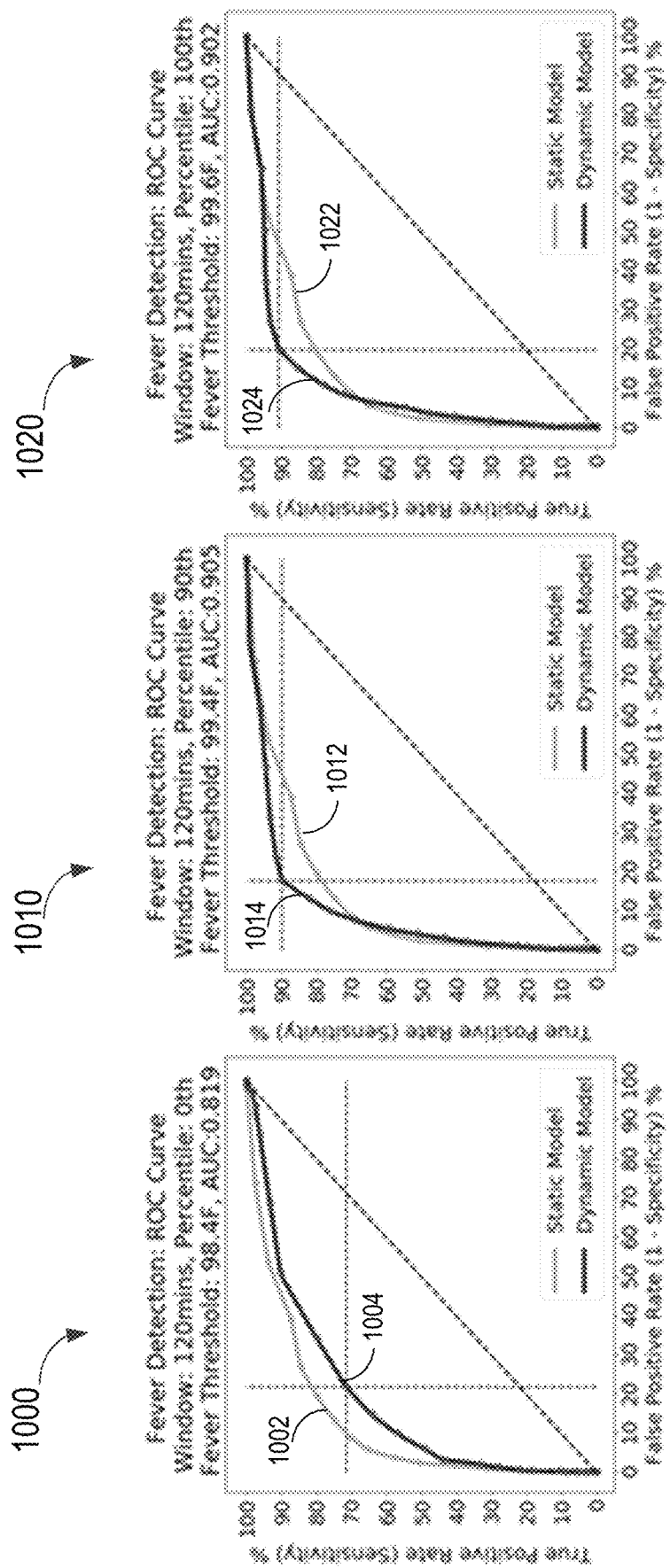
FIG. 10A includes a diagram showing examples of ROC curves for fever detection using a static fever alert model and a dynamic fever alert model according to certain embodiments.
FIG. 10B includes a diagram showing examples of ROC curves for fever detection using a static fever alert model and a dynamic fever alert model according to certain embodiments.
FIG. 10C includes a diagram showing examples of ROC curves for fever detection using a static fever alert model and a dynamic fever alert model according to certain embodiments.

FIG. 10A includes a diagram 1000 showing examples of ROC curves for fever detection using a static fever alert model and a dynamic fever alert model according to certain embodiments. In FIG. 10A, an ROC curve 1002 is generated using a static fever alert model as described above with respect to FIG. 8. An ROC curve 1004 is generated using a dynamic fever alert model where the time window is 120 minutes and the 0th percentile is used to compare against the threshold temperature. The maximum sum of sensitivity and specificity may be achieved when the threshold for high fever is set at 98.4° F.

FIG. 10B includes a diagram 1010 showing examples of ROC curves for fever detection using a static fever alert model and a dynamic fever alert model according to certain embodiments. In FIG. 10B, an ROC curve 1012 is generated using a static fever alert model as described above with respect to FIG. 8. An ROC curve 1014 is generated using a dynamic fever alert model where the time window is 120 minutes and the 90th percentile is used to compare against the threshold temperature. The maximum sum of sensitivity and specificity may be achieved when the threshold for high fever is set at 99.4° F.

FIG. 10C includes a diagram 1020 showing examples of ROC curves for fever detection using a static fever alert model and a dynamic fever alert model according to certain embodiments. In FIG. 10C, an ROC curve 1022 is generated using a static fever alert model as described above with respect to FIG. 8. An ROC curve 1024 is generated using a dynamic fever alert model where the time window is 120 minutes and the 100th percentile is used to compare against the threshold temperature. The maximum sum of sensitivity and specificity may be achieved when the threshold for high fever is set at 99.6° F.

FIGS. 10A-10C indicate that the maximum sum of sensitivity and specificity may be achieved when the 90th percentile is used to compare against a threshold temperature set to 99.4° F. Under this setting, the sensitivity of the dynamic fever alert model is about 0.89, and the specificity of the dynamic fever alert model is about 0.82.

Figure 11:
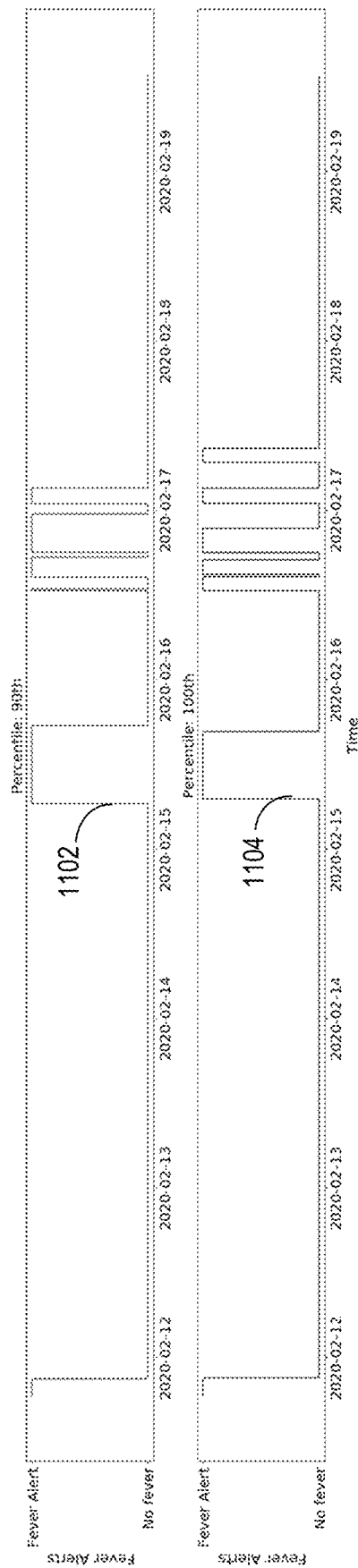
FIG. 11 illustrates examples of fever alerts generated by a dynamic fever alert model described above according to certain embodiments.

FIG. 11 illustrates examples of fever alerts generated by a dynamic fever alert model described above according to certain embodiments. The examples of fever alerts may be determined based on the estimated core body temperatures shown by curve 502. A first diagram 1102 shows the fever alerts generated by a dynamic fever alert model when the 90th percentile value in each time window is used to compare against a threshold temperature. A second diagram 1104 shows the fever alerts generated by a dynamic fever alert model when the 100th percentile value in each time window is used to compare against the threshold temperature.

As described above, the temperature at the skin surface may be lower than the core body temperature at least in part due to the thermal resistance of the skin. In certain embodiments, the thermal resistance of the skin may be determined and used to determine the core body temperature that accounts for the effects of the thermal resistance of the skin.

Figure 12A:
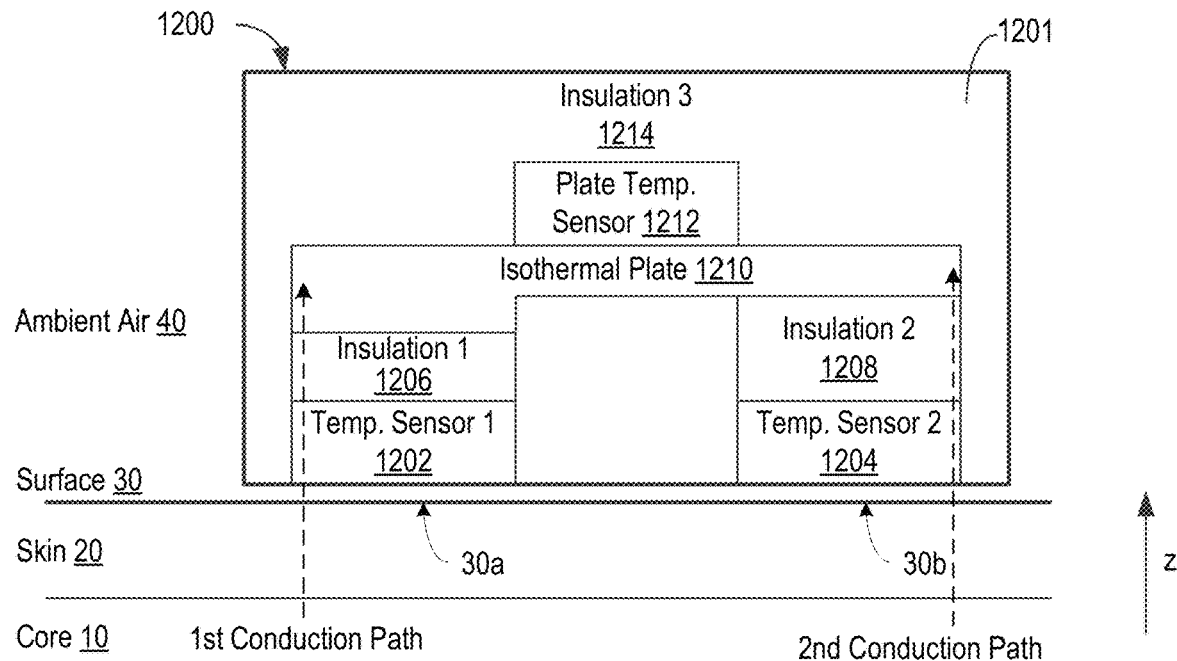
FIG. 12A illustrates an example of a temperature measurement device according to certain embodiments.
Figure 12B:
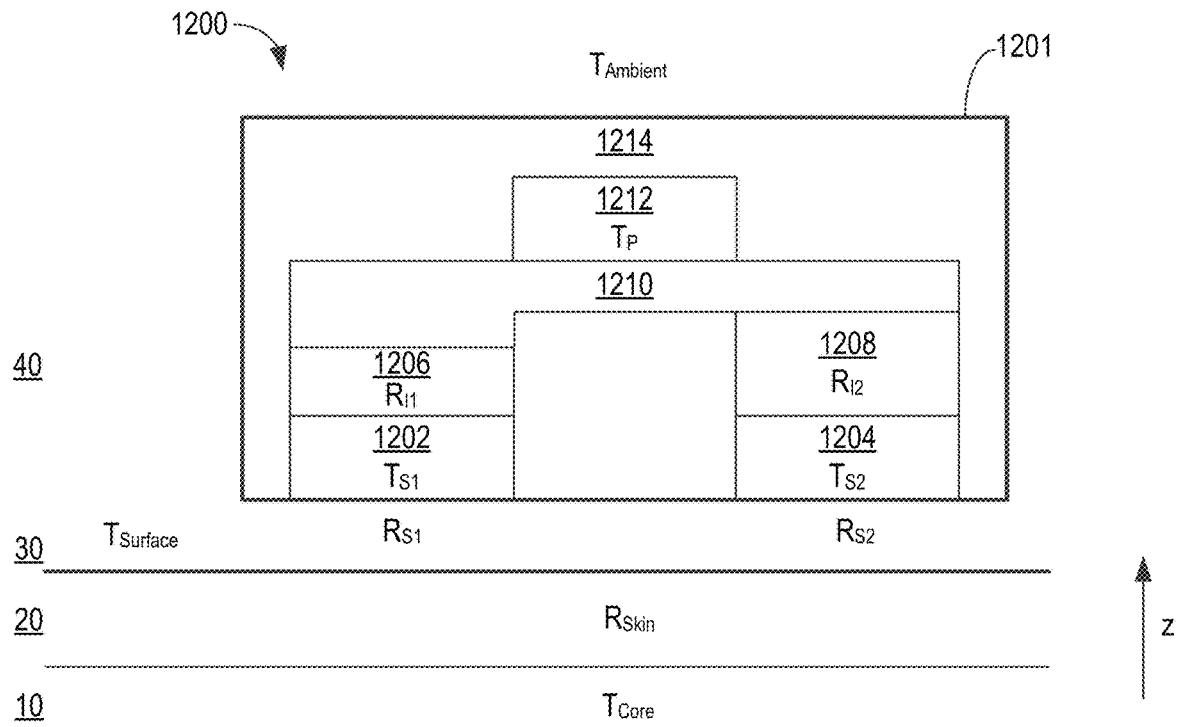
FIG. 12B illustrates an example of an electrical model of the temperature measurement device shown in FIG. 12A according to certain embodiments.

FIG. 12A illustrates an example of a temperature measurement device 1200 according to certain embodiments. FIG. 12B illustrates an example of an electrical model of temperature measurement device 1200 according to certain embodiments. temperature measurement device 1200 may include two or more skin temperature sensors that may be used to determine the thermal resistance of the skin. Temperature measurement device 1200 may be positioned on a skin surface 30 of a person's skin 20, where temperature measurement device 1200 may non-invasively and accurately determine a temperature $T_{Core}$ of the person's core 10 under skin 20.

As illustrated in FIG. 12B, skin 20 may have a thermal resistance $R_{Skin}$. A measurement of a temperature $T_{Surface}$ at skin surface 30 may not accurately reflect the temperature $T_{Core}$ at core 10, because the thermal resistance $R_{Skin}$ of the intervening layer of skin 20 may prevent effective conduction of heat from core 10 to skin surface 30. Additionally, as described above, ambient air 40 at a temperature $T_{Ambient}$ may affect the temperature $T_{Surface}$. To measure the core body temperature $T_{Core}$ accurately, temperature measurement device 1200 accounts for the effect of the thermal resistance $R_{Skin}$ of skin 20 on temperature measurements taken at skin surface 30.

As shown in FIG. 12A, temperature measurement device 1200 may include a first temperature sensor 1202 and a second temperature sensor 1204. First temperature sensor 1202 and second temperature sensor 1204 may include thermistors, whose temperature-dependent resistance can be electrically determined to measure temperature. First temperature sensor 1202 may be positioned to measure a temperature $T_{S1}$ at a first area 30a of skin surface 30. Second temperature sensor 1204 may be positioned to measure a temperature $T_{S2}$ at a second area 30b of skin surface 30, where second area 30b is spaced a distance from first area 30a. In general, first temperature sensor 1202 and second temperature sensor 1204 are spaced to allow the skin 20 to equilibrate for measurement of the temperatures at skin surface areas 30a and 30b as described herein.

As illustrated in FIG. 12B, first temperature sensor 1202 is associated with a thermal resistance $R_{S1}$. Similarly, second temperature sensor 1204 is associated with a thermal resistance $R_{S2}$. Because first temperature sensor 1202 and second temperature sensor 1204 may be similar devices applied to the skin surface 30 in a similar manner, the thermal resistances $R_{S1}$ and $R_{S2}$ may be substantially equal.

Temperature measurement device 1200 may also include a first insulation material 1206 and a second insulation material 1208. As shown, first insulation material 1206 may form a layer above first temperature sensor 1202, and second insulation material 1208 may form a layer above the second temperature sensor 1204. First temperature sensor 1202 may be disposed between first area 30a and first insulation material 1206. Second temperature sensor 1204 may be disposed between second area 30b and second insulation material 1208. First insulation material 1206 may be thermally coupled to first area 30a via first temperature sensor 1202. Second insulation material 1208 may be thermally coupled to second area 30b via second temperature sensor 1204.

As further illustrated in FIG. 12B, first insulation material 1206 may be produced to have a designed thermal resistance $R_{I1}$. Second insulation material 1208 may be produced to have a designed thermal resistance $R_{I2}$. Thermal resistance $R_{I2}$ for second insulation material 1208, however, is different from thermal resistance $R_{I1}$ for first insulation material 1206. Due to the difference in thermal resistances $R_{I1}$ and $R_{I2}$, temperature measurement device 1200 may be considered to be an asymmetric sensor.

In addition, temperature measurement device 1200 may include an isothermal plate 1210 that is thermally coupled to first insulation material 1206 and second insulation material 1208. First insulation material 1206 may be disposed between first temperature sensor 1202 and isothermal plate 1210. Similarly, second insulation material 1208 may be disposed between second temperature sensor 1204 and isothermal plate 1210. Due to its isothermal properties, isothermal plate 1210 may have a substantially uniform temperature $T_P$ at steady state. Temperature measurement device 1200 may also include a plate temperature sensor 1212 to measure a temperature $T_P$ of isothermal plate 1210. Plate temperature sensor 1212 may also include a thermistor, whose temperature-dependent resistance can be electrically determined to measure temperature.

As illustrated, on the bottom surface, first insulation material 1206 may have a temperature $T_{S1}$ as measured by first temperature sensor 1202, and on the top surface, first insulation material 1206 may have a temperature $T_P$ as measured by plate temperature sensor 1212. Meanwhile, on the bottom surface, second insulation material 1208 may have a temperature $T_{S2}$ as measured by second temperature sensor 1204, and on the top surface, second insulation material 1208 may also have a temperature $T_P$ as measured by plate temperature sensor 1212.

Temperature measurement device 1200 may include a housing 1201 that encloses first temperature sensor 1202, second temperature sensor 1204, first insulation material 1206, second insulation material 1208, isothermal plate 1210, and plate temperature sensor 1212. Temperature measurement device 1200 may also include a third insulation material 1214 that may insulate these components from heat transfer with ambient air 40. Thus, third insulation material 1214 may also reduce the effect of the ambient air 40 on the temperature measurements taken by first temperature sensor 1202 and second temperature sensor 1204 at the skin surface 30.

In operation, temperature measurement device 1200 may be placed on skin surface 30. First temperature sensor 1202 and second temperature sensor 1204 may be applied to skin surface 30 with enough pressure to help ensure full and consistent contact. Such contact helps to prevent air gaps which can introduce additional undesired thermal resistance at skin surface 30. Moreover, such contact helps to insulate first temperature sensor 1202 and second temperature sensor 1204 from undesired heat exchange with ambient air 40 and to ensure that substantially all heat exchange occurs through skin 20.

Once temperature measurement device 1200 is placed on skin surface 30, heat from core 10 may be conducted along a first conduction path and a second conduction path in the z-direction as shown in FIG. 12A. The first heat conduction path may include: (i) skin 20 at first area 30a, (ii) first temperature sensor 1202, (iii) first insulation material 1206, and (iv) isothermal plate 1210. The second heat conduction path may include: (i) skin 20 at second area 30b, (ii) second temperature sensor 1204, (iii) second insulation material 1208, and (iv) isothermal plate 1210.

After a period of time, the heat conduction from core 10 into temperature measurement device 1200 may reach a steady state. In particular, temperatures $T_{S1}$, $T_{S2}$, and $T_P$ may remain unchanged when the system reaches steady state. The temperatures $T_{S1}$, $T_{S2}$, and $T_P$ measured by the respective temperature sensors 1202, 1204, 1212 may be monitored to determine when steady state has been achieved.

Once steady state has been achieved, temperature measurement device 1200 can determine the core body temperature $T_{Core}$. The heat conduction into temperature measurement device 1200 follows Fourier's Law, which can be generally expressed as:

$$q_x = \Delta T/R \tag{1}$$

where $q_x$ is the heat transfer rate along the x-direction, $\Delta T$ is the difference in temperature between two points, and R is the thermal resistance between the two points.

For heat conduction from core 10 to isothermal plate 1210 along the first conduction path, $\Delta T$ may be given by the difference between the temperatures $T_{Core}$ and $T_P$, and R is given by the sum of the thermal resistances from core 10 to isothermal plate 1210, i.e., the thermal resistance $R_{Skin}$ from skin 20, thermal resistance $R_{S1}$ at first temperature sensor 1202, and thermal resistance $R_{I1}$ from first insulation material 1206. Thus, $$q_x(\text{core to plate, 1st path}) = (T_{Core} - T_P)/(R_{Skin} + R_{S1} + R_{I1}) \tag{2}$$

For heat conduction from first temperature sensor 1202 to isothermal plate 1210 along the first conduction path, $\Delta T$ may be given by the different between the temperatures $T_{S1}$ and $T_P$, and R may be given by the sum of the thermal resistances from first temperature sensor 1202 to isothermal plate 1210, i.e., the thermal resistance $R_{I1}$ from first insulation material 1206. Thus, $$q_x(\text{sensor to plate, 1st path}) = (T_{S1} - T_P)/R_{I1}. \tag{3}$$

At steady state, the heat transfer rate from core 10 to isothermal plate 1210 may be the same as the heat transfer rate from first temperature sensor 1202 to isothermal plate 1210. Thus, $$q_x(\text{core to plate, 1st path}) = q_x(\text{sensor to plate, 1st path}), \tag{4}$$

$$(T_{Core} - T_P)/(R_{Skin} + R_{S1} + R_{I1}) = (T_{S1} - T_P)/R_{I1}, \tag{5}$$

or, $$T_{Core} = [((R_{Skin} + R_{S1} + R_{I1})/R_{I1}) * (T_{S1} - T_P)] + T_P. \tag{6}$$

Similar calculations can be made for the second conduction path to find:

$$T_{Core} = [((R_{Skin} + R_{S2} + R_{I2})/R_{I2}) * (T_{S2} - T_P)] + T_P. \tag{7}$$

It can be assumed that the temperature $T_{Core}$ at core 10 and thermal resistance $R_{Skin}$ of skin 20 are the same for the first conduction path and the second conduction path. As such, equations (6) and (7) may be combined as a system of two equations.

As described above, temperatures $T_{S1}$, $T_{S2}$, and $T_P$ can be measured with first temperature sensor 1202, second temperature sensor 1204, and plate temperature sensor 1212, respectively. Additionally, thermal resistances $R_{I1}$ and $R_{I2}$ are known from the design of first insulation material 1206 and second insulation material 1208, respectively. Meanwhile, the following values are unknown: the core body temperature $T_{Core}$, the thermal resistance $R_{Skin}$ of skin 20, the thermal resistance $R_{S1}$ associated with first insulation material 1206, and the thermal resistance $R_{S2}$ associated with second insulation material 1208.

As also described above, the thermal resistances $R_{S1}$ and $R_{S2}$ may be substantially equal, because first temperature sensor 1202 and second temperature sensor 1204 may be similar devices applied to skin surface 30 in a similar manner. Assuming $R_{S1} = R_{S2}$, $$T_{Core} = [((R_{Skin} + R_{S1} + R_{I1})/R_{I1}) * (T_{S1} - T_P)] + T_P, \tag{8}$$

and $$T_{Core} = [((R_{Skin} + R_{S1} + R_{I2})/R_{I2}) * (T_{S2} - T_P)] + T_P. \tag{9}$$

When the term $(R_{Skin} + R_{Sensor1})$ in equations (8) and (9) is expressed as a single thermal resistance $R_{Skin+S1}$:

$$T_{Core} = [((R_{Skin+S1} + R_{I1})/R_{I1}) * (T_{S1} - T_P)] + T_P, \tag{10}$$

and $$T_{Core} = [((R_{Skin+S1} + R_{I2})/R_{I2}) * (T_{S2} - T_P)] + T_P. \tag{11}$$

Thus, the two equations (8) and (9) can be solved for the two unknown values $R_{Skin+S1}$ and $T_{Core}$.

Figure 13:
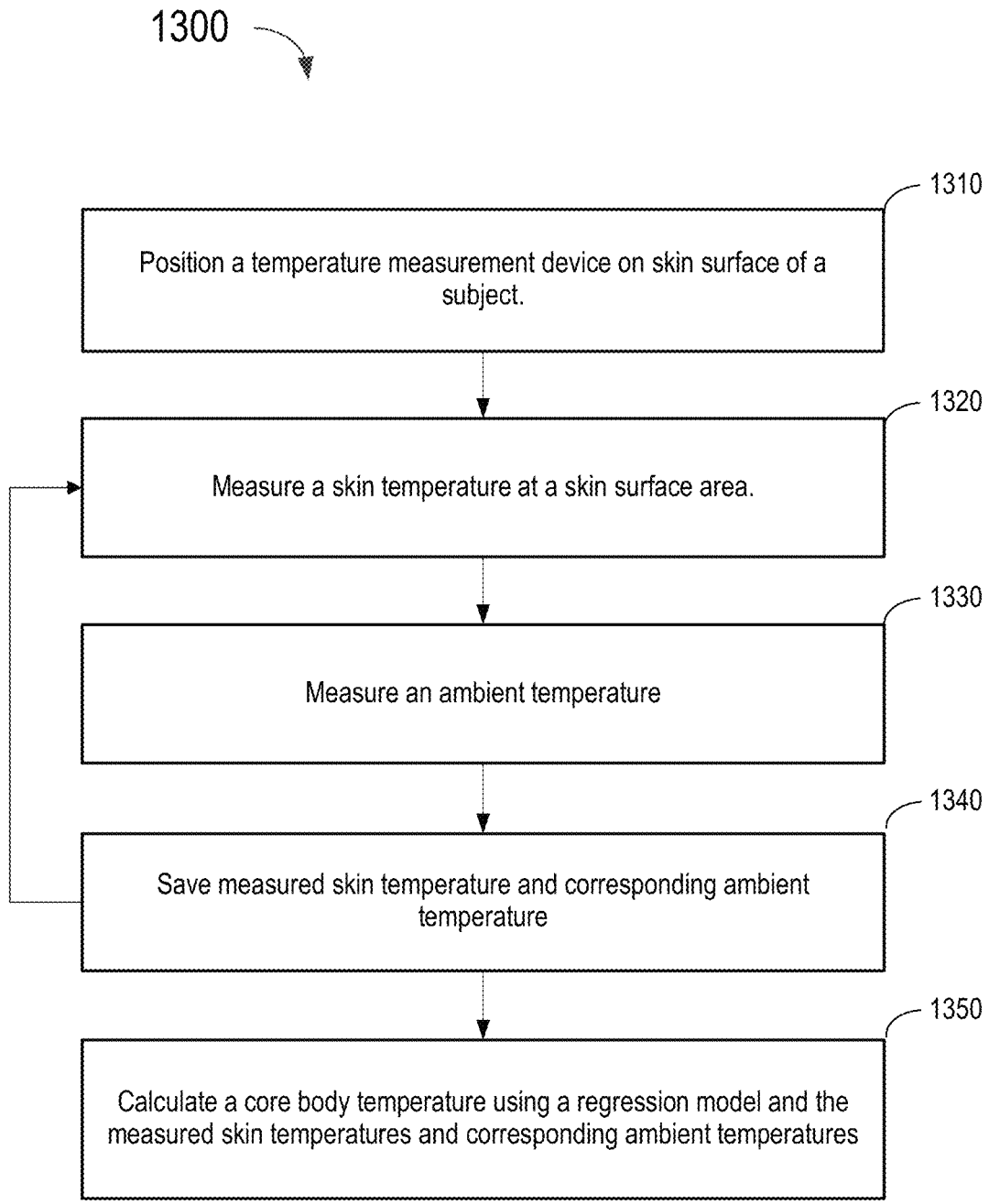
FIG. 13 is a flowchart illustrating an example of a method of estimating core body temperature according to certain embodiments.

FIG. 13 is a flowchart 1300 illustrating an example of a method of estimating core body temperature according to certain embodiments. The operations described in flowchart 1300 are for illustration purposes only and are not intended to be limiting. In various implementations, modifications may be made to flowchart 1300 to add additional operations or to omit some operations. The operations described in flowchart 1300 may be performed by, for example, the temperature measurement devices described above with respect to, for example, FIGS. 1, 2, 7A-7D, and 12A-12B.

At block 1310, a temperature measurement device, such as temperature measurement device 100, may be positioned on a skin surface of a subject as shown in, for example, FIG. 1, FIGS. 7A-7D, and FIGS. 12A-12B. The temperature measurement device may include one or more skin temperature sensors and one or more ambient temperature sensors. The one or more skin temperature sensors and the one or more ambient temperature sensors may be insulated by a thermal insulation material.

At block 1320, the one or more skin temperature sensors may measure a skin temperature at a skin surface area at a time instant. At block 1330, the one or more ambient temperature sensors may measure an ambient temperature at the time instant. At block 1340, the measured skin temperature and corresponding ambient temperature may be saved to a memory device. The operations at blocks 1320-1340 may be repeated for a plurality of times at a plurality of time instants to measure a plurality of skin temperatures and a plurality of ambient temperature.

At block 1350, a controller (e.g., controller 114 or 220) a processing unit may estimate a current core body temperature using a prediction model and the measured plurality of skin temperatures and corresponding ambient temperatures that include past measurement results. The prediction model may include a regression model that includes a set of regressors and corresponding weights. The regression model may include, for example, a nonlinear autoregressive exogenous (NARX) model. The set of regressors of the regression model may include skin temperatures and ambient temperatures measured at two or more past time instants, and/or each of the plurality of skin temperatures and the plurality of ambient temperatures raised to powers of two or more values. The weights of the regression model may be trained to minimize the mean square error (MSE).

In some embodiments, the number of time instants in the plurality of time instants, the degree of polynomial in the regression model, and/or the measurement frequency of the first temperature sensor may be dynamically tuned based on external instructions. In some embodiments, the body temperature of the subject estimated by the controller may be displayed to a user. In some embodiments, a signal indicating a high temperature event may be generated based on the body temperature of the subject. For example, an alarming sound or light signal may be generated.

Figure 14:
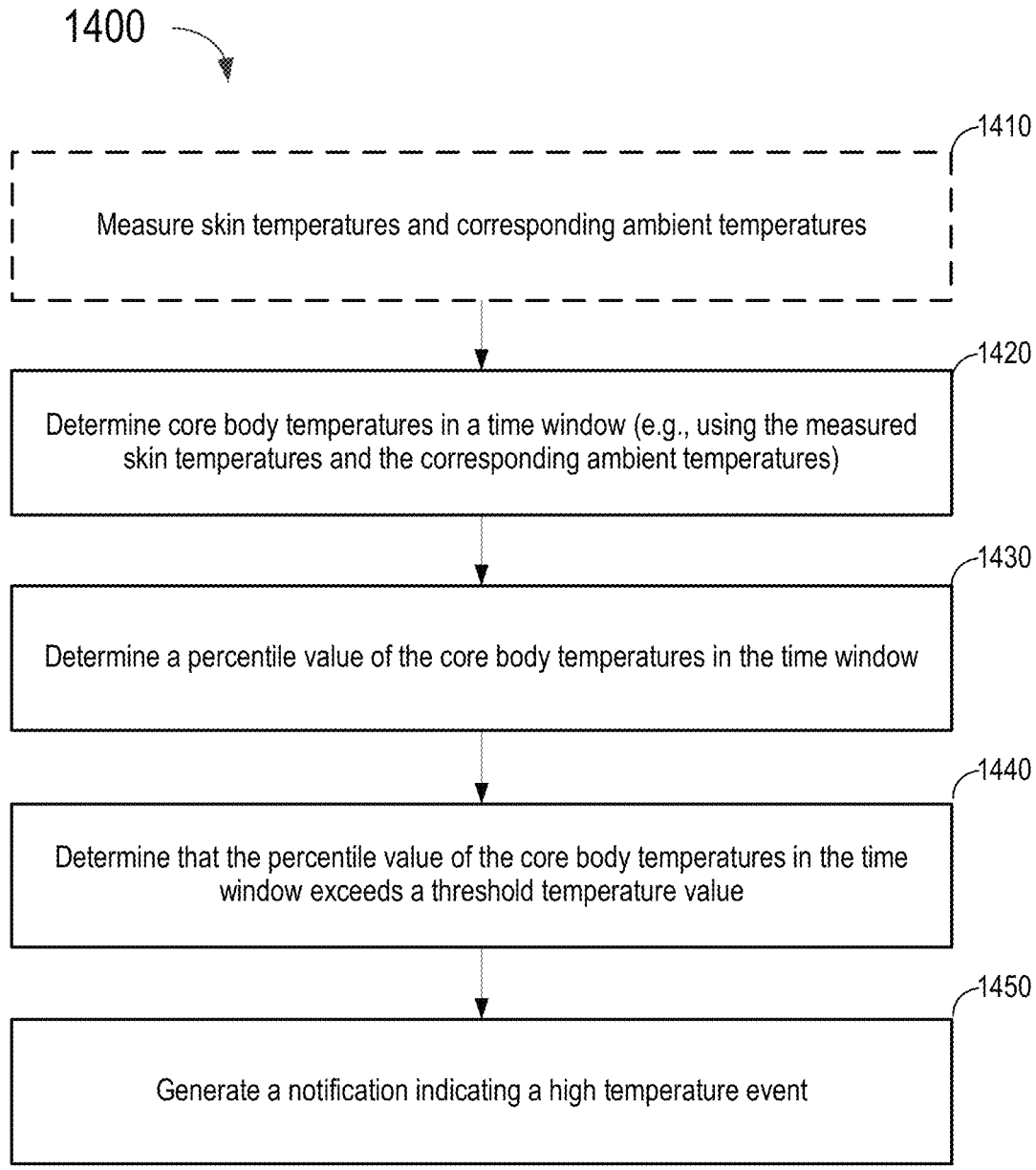
FIG. 14 is a flowchart illustrating an example of a method of generating fever alerts based on estimated core body temperatures according to certain embodiments.

FIG. 14 is a flowchart 1400 illustrating an example of a method of generating fever alerts based on estimated core body temperatures according to certain embodiments. The operations described in flowchart 1400 are for illustration purposes only and are not intended to be limiting. In various implementations, modifications may be made to flowchart 1400 to add additional operations or to omit some operations. The operations described in flowchart 1400 may be performed by, for example, the temperature measurement devices described above with respect to, for example, FIGS. 1, 2, 7A-7D, and 12A-12B.

Optionally, at block 1410, a plurality of skin temperatures and corresponding ambient temperatures may be measured as described with respect to, for example, blocks 1320-1340 of FIG. 13. At block 1420, core body temperatures in a time window may be determined, for example, using the measured skin temperatures and the corresponding ambient temperatures as described above with respect to, for example, block 1350 of FIG. 13. In some embodiments, the core body temperatures in the time window may be determined, additionally or alternatively, using the temperature measurement device and method described above with respect to FIGS. 12A and 12B.

At block 1430, a percentile value of the core body temperatures in the time window may be determined. For example, a 0%, 90%, or 100% percentile value may be determined for core body temperatures in the time window.

At block 1440, the percentile value of the core body temperatures in the time window may be compared against a threshold temperature value.

At block 1450, a notification indicating a high temperature event may be generated when the percentile value of the core body temperatures in the time window is greater than the threshold temperature value. The notification may include, for example, an alarming sound or light signal, or an electrical signal to a user device.

In some embodiments, the duration of the time window, the first percentile, the threshold temperature value, and/or the measurement frequency of the temperature measurement device may be dynamically tuned through a user interface device and a controller.

FIG. 15 illustrates an example of an electronic system 1500 of a temperature measurement device according to certain embodiments. In this example, electronic system 1500 may include one or more processor(s) 1510 (or controllers, such as microcontrollers) and a memory 1520. Processor(s) 1510 may include, for example, an ARM® or MIPS® processor, a microcontroller, or an application specific integrated circuit (ASIC). Processor(s) 1510 may be configured to execute instructions for performing operations at a number of components, and can be, for example, a general-purpose processor or microprocessor suitable for implementation within a portable electronic device. Processor(s) 1510 may be communicatively coupled with a plurality of components within electronic system 1500 through a bus 1505. Bus 1505 may be any subsystem adapted to transfer data within electronic system 1500. Bus 1505 may include a plurality of computer buses and additional circuitry to transfer data.

Memory 1520 may be coupled to processor(s) 1510 directly or through bus 1505. In some embodiments, memory 1520 may offer both short-term and long-term storage and may be divided into several units. Memory 1520 may be volatile, such as static random access memory (SRAM) and/or dynamic random access memory (DRAM), and/or non-volatile, such as read-only memory (ROM), flash memory, and the like. Furthermore, memory 1520 may include removable storage devices, such as secure digital (SD) cards. Memory 1520 may provide storage of computer-readable instructions, data structures, program modules, and other data for electronic system 1500. In some embodiments, memory 1520 may be distributed into different hardware modules. A set of instructions and/or code might be stored on memory 1520. The instructions might take the form of executable code that may be executable by electronic system 1500, and/or might take the form of source and/or installable code, which, upon compilation and/or installation on electronic system 1500 (e.g., using any of a variety of generally available compilers, installation programs, compression/decompression utilities, etc.), may take the form of executable code.

In some embodiments, memory 1520 may store a plurality of application modules 1524, which may include any number of applications. Examples of applications may include applications associated with different sensors to perform different functions. In some embodiments, certain applications or parts of application modules 1524 may be executable by other hardware modules. In certain embodiments, memory 1520 may additionally include secure memory, which may include additional security controls to prevent copying or other unauthorized access to secure information.

In some embodiments, memory 1520 may include a light-weight operating system 1522 loaded therein. Operating system 1522 may be operable to initiate the execution of the instructions provided by application modules 1524 and/or manage other hardware modules as well as interfaces with a wireless communication subsystem 1530 which may include one or more wireless transceivers. Operating system 1522 may be adapted to perform other operations across the components of electronic system 1500 including threading, resource management, data storage control and other similar functionality. Operating system 1522 may include various light-weight operating systems, such as operating systems used in internet-of-thing devices.

Wireless communication subsystem 1530 may include, for example, an infrared communication device, a wireless communication device and/or chipset (such as a Bluetooth® device, a BLE device, a ZigBee device, an IEEE 802.11 device, a Wi-Fi device, a WiMax device, a near-field communication (NFC) device, etc.), and/or similar communication interfaces. Electronic system 1500 may include one or more antennas 1534 for wireless communication as part of wireless communication subsystem 1530 or as a separate component coupled to any portion of the system. Depending on the desired functionality, wireless communication subsystem 1530 may include separate transceivers to communicate with base transceiver stations and other wireless devices and access points, which may include communicating with different data networks and/or network types, such as wireless wide-area networks (WWANs), wireless local area networks (WLANs), or wireless personal area networks (WPANs). A WWAN may be, for example, a WiMax (IEEE 1502.16) network. A WLAN may be, for example, an IEEE 802.11x network. A WPAN may be, for example, a Bluetooth network, an IEEE 802.15x network, or some other types of network. The techniques described herein may also be used for any combination of WWAN, WLAN, and/or WPAN. Wireless communications subsystem 1530 may permit data to be exchanged with a network, other computer systems, and/or any other devices described herein. Wireless communication subsystem 1530 may include a means for transmitting or receiving data, such as various sensor data, using antenna(s) 1534. Wireless communication subsystem 1530, processor(s) 1510, and memory 1520 may together comprise at least a part of one or more means for performing some functions disclosed herein.

Embodiments of electronic system 1500 may also include one or more sensors 1540. Sensors 1540 may include, for example, an image sensor, an accelerometer, a pressure sensor, a temperature sensor, a humidity sensor, a proximity sensor, a magnetometer, a gyroscope, an inertial sensor (e.g., a module that includes an accelerometer and a gyroscope), an ambient light sensor, or any other module operable to provide sensory output and/or receive sensory input. These sensors may be implemented using various technologies known to a person skilled in the art. For example, the accelerometer may be implemented using piezoelectric, piezo-resistive, capacitive, or micro electro-mechanical systems (MEMS) components, and may include a two-axis or multiple-axis accelerometer. In some embodiments, electronic system 1500 may include a datalogger, which may record the information detected by the sensors.

Electronic system 1500 may include an input/output module 1550. Input/output module 1550 may include one or more input devices or output devices. Examples of the input devices may include a touch pad, microphone(s), button(s), dial(s), switch(es), a port (e.g., micro-USB port) for connecting to a peripheral device (e.g., a mouse or controller), or any other suitable device for controlling electronic system 1500 by a user. In some implementations, input/output module 1550 may include an output device, such as a photodiode or a light-emitting diode (LED) that can be used to generate a signaling light beam, such as an alarm signal.

Electronic system 1500 may include a power subsystem that may include one or more rechargeable or non-rechargeable batteries 1570, such as alkaline batteries, lead-acid batteries, lithium-ion batteries, zinc-carbon batteries, and NiCd or NiMH batteries. The power subsystem may also include one or more power management circuits 1560, such as voltage regulators, DC-to-DC converters, wired (e.g., universal serial bus (USB) or micro USB) or wireless (NFC or Qi) charging circuits, energy harvest circuits, and the like.

The devices, systems, modules, components, and methods discussed above are examples only. Various embodiments may omit, substitute, or add various procedures or components as appropriate. Also, features described with respect to certain embodiments may be combined in various other embodiments. Different aspects and elements of the embodiments may be combined in a similar manner. Also, technology evolves and, thus, many of the elements are examples that do not limit the scope of the disclosure to those specific examples.

Specific details are given in the description to provide a thorough understanding of the embodiments. However, embodiments may be practiced without these specific details. For example, well-known circuits, processes, systems, structures, and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing various embodiments. Various changes may be made in the function and arrangement of elements without departing from the spirit and scope of the present disclosure.

Also, some embodiments were described as processes depicted as flow diagrams or block diagrams. Although each may describe the operations as a sequential process, many of the operations may be performed in parallel or concurrently. In addition, the order of the operations may be rearranged. A process may have additional steps not included in the figure. Furthermore, embodiments of the methods may be implemented by hardware, software, firmware, middleware, microcode, hardware description languages, or any combination thereof. When implemented in software, firmware, middleware, or microcode, the program code or code segments to perform the associated tasks may be stored in a computer-readable medium such as a storage medium. Processors may perform the associated tasks.

It will be apparent to those skilled in the art that substantial variations may be made in accordance with specific requirements. For example, customized or special-purpose hardware might also be used, and/or particular elements might be implemented in hardware, software (including portable software, such as applets, etc.), or both. Further, connection to other computing devices such as network input/output devices may be employed.

With reference to the appended figures, components that can include memory can include non-transitory machine-readable media. The term "machine-readable medium" and "computer-readable medium" may refer to any storage medium that participates in providing data that causes a machine to operate in a specific fashion. In embodiments provided hereinabove, various machine-readable media might be involved in providing instructions/code to processing units and/or other device(s) for execution. Additionally or alternatively, the machine-readable media might be used to store and/or carry such instructions/code. In many implementations, a computer-readable medium is a physical and/or tangible storage medium. Such a medium may take many forms, including, but not limited to, non-volatile media, volatile media, and transmission media. Common forms of computer-readable media include, for example, magnetic and/or optical media such as compact disk (CD) or digital versatile disk (DVD), punch cards, paper tape, any other physical medium with patterns of holes, a RAM, a programmable read-only memory (PROM), an erasable programmable read-only memory (EPROM), a FLASH-EPROM, any other memory chip or cartridge, a carrier wave as described hereinafter, or any other medium from which a computer can read instructions and/or code. A computer program product may include code and/or machine-executable instructions that may represent a procedure, a function, a subprogram, a program, a routine, an application (App), a subroutine, a module, a software package, a class, or any combination of instructions, data structures, or program statements.

Those of skill in the art will appreciate that information and signals used to communicate the messages described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Terms, "and" and "or" as used herein, may include a variety of meanings that are also expected to depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein may be used to describe any feature, structure, or characteristic in the singular or may be used to describe some combination of features, structures, or characteristics. However, it should be noted that this is merely an illustrative example and claimed subject matter is not limited to this example.

Furthermore, the term "at least one of" if used to associate a list, such as A, B, or C, can be interpreted to mean any combination of A, B, and/or C, such as A, AB, AC, BC, AA, ABC, AAB, AABBCCC, etc.

Further, while certain embodiments have been described using a particular combination of hardware and software, it should be recognized that other combinations of hardware and software are also possible. Certain embodiments may be implemented only in hardware, or only in software, or using combinations thereof. In one example, software may be implemented with a computer program product containing computer program code or instructions executable by one or more processors for performing any or all of the steps, operations, or processes described in this disclosure, where the computer program may be stored on a non-transitory computer readable medium. The various processes described herein can be implemented on the same processor or different processors in any combination.

Where devices, systems, components or modules are described as being configured to perform certain operations or functions, such configuration can be accomplished, for example, by designing electronic circuits to perform the operation, by programming programmable electronic circuits (such as microprocessors) to perform the operation such as by executing computer instructions or code, or processors or cores programmed to execute code or instructions stored on a non-transitory memory medium, or any combination thereof. Processes can communicate using a variety of techniques, including, but not limited to, conventional techniques for inter-process communications, and different pairs of processes may use different techniques, or the same pair of processes may use different techniques at different times.

The specification and drawings are, accordingly, to be regarded in an illustrative rather than a restrictive sense. It will, however, be evident that additions, subtractions, deletions, and other modifications and changes may be made thereunto without departing from the broader spirit and scope as set forth in the claims. Thus, although specific embodiments have been described, these are not intended to be limiting. Various modifications and equivalents are within the scope of the following claims.

What is claimed is:

1. A temperature measurement device for determining a body temperature of a subject, the temperature measurement device comprising:
    a first temperature sensor configured to measure a plurality of skin temperatures of the subject at a plurality of time instants;
    a second temperature sensor spaced apart from the first temperature sensor and configured to measure a plurality of ambient temperatures at the plurality of time instants;
    a thermal insulation material between the first temperature sensor and the second temperature sensor;
    a memory device configured to store the plurality of skin temperatures and the plurality of ambient temperatures; and
    a controller configured to estimate, using a regression model, the body temperature of the subject based on the plurality of skin temperatures and the plurality of ambient temperatures, wherein the regression model includes a nonlinear autoregressive exogenous (NARX) model.

2. The temperature measurement device of claim 1, further comprising a user interface device configured to display the body temperature of the subject estimated by the controller or generate a signal indicating a high temperature event based on the body temperature of the subject.

3. The temperature measurement device of claim 1, wherein the temperature measurement device is in a form of a wearable device or is embedded in a garment.

4. The temperature measurement device of claim 1, wherein the temperature measurement device further comprises a third temperature sensor spaced apart from the first temperature sensor and configured to measure a second plurality of skin temperatures of the subject at the plurality of time instants.

5. The temperature measurement device of claim 1, wherein
the regression model includes a set of regressors and corresponding weights.

6. The temperature measurement device of claim 5, wherein the set of regressors of the regression model includes skin temperatures and ambient temperatures measured at two or more past time instants.

7. The temperature measurement device of claim 5, wherein the set of regressors of the regression model includes each of the plurality of skin temperatures and the plurality of ambient temperatures raised to powers of two or more values.

8. The temperature measurement device of claim 5, wherein the weights of the regression model are trained to minimize a mean square error.

9. The temperature measurement device of claim 5, further comprising a user interface device configured to receive at least one of:
a number of time instants in the plurality of time instants;
a degree of polynomial in the regression model; or
a measurement frequency of the first temperature sensor.

10. The temperature measurement device of claim 9, wherein the controller is further configured to set the measurement frequency of the first temperature sensor.

11. A method of determining a body temperature of a subject, the method comprising:
measuring, by a first temperature sensor, a plurality of skin temperatures of the subject at a plurality of time instants;
measuring, by a second temperature sensor spaced apart from the first temperature sensor, a plurality of ambient temperatures at the plurality of time instants;
storing the plurality of skin temperatures and the plurality of ambient temperatures in a memory device;
obtaining, by a controller from the memory device, the plurality of skin temperatures and the plurality of ambient temperatures; and
determining, by the controller based on a regression prediction-model, the body temperature of the subject based on the plurality of skin temperatures and the plurality of ambient temperatures, wherein the regression model includes a nonlinear autoregressive exogenous (NARX) model.

12. The method of claim 11, further comprising at least one of:
displaying the body temperature of the subject determined by the controller; or
generating a signal indicating a high temperature event based on the body temperature of the subject.

13. The method of claim 11, wherein the regression model includes a set of regressors and corresponding weights.

14. The method of claim 13, wherein the set of regressors of the regression model includes skin temperatures and ambient temperatures measured at two or more past time instants.

15. The method of claim 13, wherein the set of regressors of the regression model includes each of the plurality of skin temperatures and the plurality of ambient temperatures raised to powers of two or more values.

16. The method of claim 13, further comprising receiving, by a user interface device, at least one of:
a number of time instants in the plurality of time instants;
a degree of polynomial in the regression model; or
a measurement frequency of the first temperature sensor.

17. A non-transitory computer-readable storage medium storing instructions executable by one or more processors, the instructions, when executed by the one or more processors, cause the one or more processors to perform operations including:
obtaining a plurality of skin temperatures of a subject measured at a plurality of time instants;
obtaining a plurality of ambient temperatures measured at the plurality of time instants; and
determining, based on a regression model that includes a set of regressors and corresponding weights, a body temperature of the subject based on the plurality of skin temperatures and the plurality of ambient temperatures, wherein the regression model includes a nonlinear autoregressive exogenous (NARX) model.

18. The non-transitory computer-readable storage medium of claim 17, wherein:
the set of regressors of the regression model includes skin temperatures and ambient temperatures measured at two or more past time instants; and
the set of regressors of the regression model includes each of the plurality of skin temperatures and the plurality of ambient temperatures raised to powers of two or more values.

* * * * *